(12) United States Patent
Myrden et al.

(10) Patent No.: US 11,402,905 B2
(45) Date of Patent: Aug. 2, 2022

(54) EEG BRAIN-COMPUTER INTERFACE PLATFORM AND PROCESS FOR DETECTION OF CHANGES TO MENTAL STATE

(71) Applicant: HOLLAND BLOORVIEW KIDS REHABILITATION HOSPITAL, Toronto (CA)

(72) Inventors: Andrew Myrden, Toronto (CA); Thomas Tak Kin Chau, Toronto (CA)

(73) Assignee: HOLLAND BLOORVIEW KIDS REHABILITATION HOSPITAL, Toronto (CA)

( * ) Notice: Subject to any disclaimer, the term of this patent is extended or adjusted under 35 U.S.C. 154(b) by 712 days.

(21) Appl. No.: 15/865,794

(22) Filed: Jan. 9, 2018

(65) Prior Publication Data
US 2019/0212816 A1    Jul. 11, 2019

(51) Int. Cl.
*A61B 5/16*        (2006.01)
*A61B 5/378*       (2021.01)
(Continued)

(52) U.S. Cl.
CPC .............. *G06F 3/015* (2013.01); *A61B 5/369* (2021.01); *A61B 5/378* (2021.01); *A61B 5/165* (2013.01); *A61B 5/7257* (2013.01)

(58) Field of Classification Search
None
See application file for complete search history.

(56) References Cited

U.S. PATENT DOCUMENTS

| 5,447,166 A * | 9/1995 | Gevins | A61B 5/0484 |
| | | | 600/544 |
| 2009/0069707 A1* | 3/2009 | Sandford | A61B 5/165 |
| | | | 600/545 |

(Continued)

FOREIGN PATENT DOCUMENTS

WO    WO-2017040417 A1 *   3/2017   ............. A61B 5/168

OTHER PUBLICATIONS

Joseph N. Mak and Jonathan R. Wolpaw, "Clinical applications of brain-computer interfaces: Current state and future prospects," IEEE Reviews in Biomedical Engineering, vol. 2, pp. 187-199, 2009.

(Continued)

*Primary Examiner* — Etsub D Berhanu
(74) *Attorney, Agent, or Firm* — Norton Rose Fulbright Canada LLP

(57) ABSTRACT

A system for a brain-computer interface (BCI) is provided. The system comprises an output unit configured to trigger a series of mental tasks for the patient, a device having a plurality of electrodes to continuously capture real-time raw electroencephalography (EEG) data from a patient, a server, and a display device to display and update an interface with visual elements based on issued control commands from the server. The server has an acquisition unit configured to receive the electrode data, a processor configured to detect real-time changes in brain-state of the patient in response to the series of mental tasks for the patient, a presentation unit configured to generate visual elements for an interface in real-time, and a display controller configured to issue control commands to update the interface using the generated visual elements. The processor detects the real-time changes in brain-state using the electrode data. The processor is configured to generate a set of features based upon a frequency domain analysis of the EEG data, reduce the (Continued)

dimensionality of the set of features by implementing a feature clustering process to account for redundancy in EEG signal features of the EEG data, and classify the features into a mental state.

10 Claims, 20 Drawing Sheets

(51) Int. Cl.
*G06F 3/01* (2006.01)
*A61B 5/369* (2021.01)
*A61B 5/00* (2006.01)

(56) References Cited

U.S. PATENT DOCUMENTS

| | | | | |
|---|---|---|---|---|
| 2016/0113539 | A1* | 4/2016 | Sinharay | A61B 5/7253 600/544 |
| 2017/0112406 | A1* | 4/2017 | Li | A61B 5/7203 |
| 2017/0229037 | A1* | 8/2017 | Gazzaley | G09B 19/003 |
| 2019/0038166 | A1* | 2/2019 | Tavabi | A61B 5/168 |
| 2019/0110726 | A1* | 4/2019 | Chatterjee | A61B 5/0205 |
| 2019/0216392 | A1* | 7/2019 | Bower | A61B 5/0533 |

OTHER PUBLICATIONS

J. D. R. Millan et al., "Combining brain-computer interfaces and assistive technologies: State-of-the-art and challenges," Frontiers in Neuroscience., vol. 4, Article 161, pp. 1-15, Sep. 2010.

Marcel Van Gerven et al., "The brain-computer interface cycle," Journal of Neural Engineering., vol. 6, No. 041001, pp. 1-10, Jul. 22, 2009.

Eric C Leuthardt et al., "A brain-computer interface using electrocorticographic signals in humans," Journal of Neural Engineering., vol. 1, No. 2, p. 63, 2004.

Florin Popescu et al., "Single trial classification of motor imagination using 6 dry EEG electrodes," PLoS ONE, vol. 2, No. 7, p. e637, 2007.

Sarah D. Power et al., "Classification of prefrontal activity due to mental arithmetic and music imagery using hidden Markov models and frequency domain near-infrared spectroscopy," Journal of Neural Engineering, vol. 7, No. 2, p. 026002, 2010.

Andrew J. B. Myrden et al., "A brain-computer interface based on bilateral transcranial Doppler ultrasound," PLoS ONE, vol. 6, No. 9, p. e24170, 2011.

S. G. Mason et al., "A comprehensive survey of brain interface technology designs," Annals of Biomedical Engineering, vol. 35, No. 2, pp. 137-169, Feb. 2007.

Anton Nijholt and Desney Tan, "Brain-computer interfacing for intelligent systems," IEEE Intelligent Systems, vol. 23, No. 3, pp. 72-79, May/Jun. 2008.

Edward Cutrell and Desney Tan, "BCI for passive input in HCI," in Proc. CHI, vol. 8. Apr. 2008, pp. 1-3.

Thorsten O. Zander and Sabine Jatzev, "Detecting affective covert user states with passive brain-computer interfaces," in Proc IEEE 3rd Int. Conf. Affective Comput. Intell. Interact. Workshops (ACII), Sep. 2009, pp. 1-9.

Thorsten O. Zander and Christian Kothe, "Towards passive brain-computer interfaces: Applying brain-computer nterface technology to human-machine systems in general," Journal of Neural Engineering, vol. 8, No. 2, p. 025005, 2011.

Klaus-Robert Muller et al., "Machine learning for real-time single-trial EEGanalysis: From brain-computer interfacing to mental state monitoring," Journal of Neuroscience Methods, vol. 167, No. 1, pp. 82-90, 2008.

Stephen H. Fairclough, "Fundamentals of physiological computing," Interacting with Computers, vol. 21, No. 1, pp. 133-145, 2009.

T O Zander and S Jatzev, "Context-aware brain-computer interfaces: Exploring the information space of user, technical system and environment," Journal of Neural Engineering, vol. 9, No. 1, p. 016003, 2012.

Eleanor A. Curran and Maria J. Stokes, "Learning to control brain activity: A review of the production and control of EEG components for driving brain-computer interface (BCI) systems," Brain and Cognition, vol. 51, No. 3, pp. 326-336, 2003.

Boris Reuderink et al., "Affective pacman: A frustrating game for brain-computer interface experiments," in Proc. Intell. Conf. Technol. Interact. Entertainment, 2009, pp. 221-227.

Romy Lorenz et al., "Towards a holistic assessment of the user experience with hybrid BCIs," Journal of Neural Engineering, vol. 11, No. 3, p. 035007, 2014.

Kai-Quan Shen et al., "EEG-based mental fatigue measurement using multi-class support vector machines with confidence estimate," Clinical Neurophysiology, vol. 119, No. 7, pp. 1524-1533, 2008.

Leonard J. Trejo et al., "Measures and models for predicting cognitive fatigue," in Proc. Secur. Int. Soc. Opt. Photon. 2005, pp. 105-115.

Saroj K.L. Lal and Ashley Craig, "Reproducibility of the spectral components of the electroencephalogram during driver fatigue," International Journal of Psychophysiology, vol. 55, No. 2, pp. 137-143, 2005.

Budi Thomas Jap et al., "Using EEG spectral components to assess algorithms for detecting fatigue," Expert Systems with Applications, vol. 36, No. 2, pp. 2352-2359, 2009.

Chong Zhang et al., "Automatic recognition of cognitive fatigue from physiological indices by using wavelet packet transform and kernel learning algorithms," Expert Systems with Applications, vol. 36, No. 3, pp. 4664-4671, 2009.

Brahim Hamadicharef et al., "Learning EEG-based spectral-spatial patterns for attention level measurement," in Proc. IEEE Int. Symp. Circuits Syst. (ISCAS), May 2009, pp. 1465-1468.

Ning-Han Liu et al., "Recognizing the degree of human attention using EEG signals from mobile sensors," Sensors, vol. 13, No. 8, p. 10273-10286, 2013.

Chris Berka et al., "EEG correlates of task engagement and mental workload in vigilance, learning, and memory tasks," Aviation, Space, and Environmental Medicine., vol. 78, No. 5, pp B231-B244, May 2007.

Pramila Rani et al., "Anxiety-based affective communication for implicit human—Machine interaction," Advanced Engineering Informatics, vol. 21, No. 3, pp. 323-334, 2007.

David Watson and Lee Anna Clark, "The PANAS-X: Manual for the positive and negative affect schedule-expanded form," Tech. Rep., 1999.

Richard W. Homan et al., "Cerebral location of international 10-20 system electrode placement," Electroencephalography and Clinical Neurophysiology, vol. 66, No. 4, pp. 376-382, 1987.

Andrea Mognon et al., "Adjust: An automatic EEG artifact detector based on the joint use of spatial and temporal features," Psychophysiology, vol. 48, No. 2, pp. 229-240, 2011.

Andrew Myrden and Tom Chau, "Feature clustering for robust frequencydomain classification of EEG activity," Journal of Neuroscience Methods, vol. 262, pp. 77-84, 2016.

Lei Yu and Huan Liu, "Feature selection for high-dimensional data: A fast correlation-based filter solution," Proceedings of the Twentieth ICML, vol. 3. Aug. 2003, pp. 856-863.

F. Lotte et al., "A review of classification algorithms for EEG-based brain-computer interfaces," Journal of Neural Engineering, vol. 4, No. 2, p. R1, 2007.

Gustavo E.A.P.A. Batista et al., "A study of the behavior of several methods for balancing machine learning training data," ACM Sigkdd Explorations Newslett, vol. 6, No. 1, pp. 20-29, 2004.

B. Blankertz, S. Lemm, M. Treder, S. Haufe, and K.-R. Müller, "Singletrial analysis and classification of ERP components—A tutorial," NeuroImage, vol. 56, No. 2, pp. 814-825, 2011.

Klaus-Robert Muller et al., "An introduction to kernel-based learning algorithms," IEEE Transactions of Neural Networks, vol. 12, No. 2, pp. 181-201, Mar. 2001.

(56) References Cited

OTHER PUBLICATIONS

I. Rish, "An empirical study of the naive Bayes classifier," in Proc. Workshop Empirical Methods Artif. Intell. (IJCAI), New York, NY, USA, 2001, vol. 3. No. 22, pp. 41-46.

Martin Billinger et al., "Is it significant? Guidelines for reporting BCI performance," in Towards Practical Brain-Computer Interfaces. Springer, 2012, pp. 333-354.

Stefan Haufe et al., "On the interpretation of weight vectors of linear models in multivariate neuroimaging," NeuroImage, vol. 87, pp. 96-110, Feb. 2014.

Pradeep Shenoy et al., "Towards adaptive classification for BCI," Journal of Neural Engineering, vol. 3, No. 1, p. R13, 2006.

Adam Hampshire et al., "Network mechanisms of intentional learning," NeuroImage, vol. 127, pp. 123-134, Feb. 2016.

Leonard J. Trejo et al., "EEG-based estimation of mental fatigue: Convergent evidence for a three-state model," in Foundations of Augmented Cognition. Springer, 2007, pp. 201-211.

Saroj K. L. Lal and Ashley Craig, "A critical review of the psychophysiology of driver fatigue," Biological Psychology, vol. 55, No. 3, pp. 173-194, Feb. 2001.

Arjen M. Strijkstra et al., "Subjective sleepiness correlates negatively with global alpha (8-12 Hz) and positively with central frontal theta (4-8 Hz) frequencies in the human resting awake electroencephalogram," Neuroscience Letters, vol. 340, No. 1, pp. 17-20, 2003.

Birgit Abler et al., "Neural correlates of frustration," Neuroreport, vol. 16, No. 7, pp. 669-672, 2005.

Brendan A. Rich et al., "A preliminary study of the neural mechanisms of frustration in pediatric bipolar disorder using magnetoencephalography," Depression and Anxiety, vol. 27, No. 3, pp. 276-286, 2010.

Christen M. Deveney et al., "Neural mechanisms of frustration in chronically irritable children," Am. J. Psychiatry, vol. 170, No. 10, pp. 1186-1194, 2013.

Dameron S. Carter et al., "Anterior cingulate cortex, error detection, and the online monitoring of performance," Science, vol. 280, No. 5364, pp. 747-749, 1998.

Martin Spuler and Christian Niethammer, "Error-related potentials during continuous feedback: Using EEG to detect errors of different type and severity," Frontiers in Human Neuroscience, vol. 9, p. 155, Mar. 2015.

Adrien Martel et al., "EEG predictors of covert vigilant attention," Journal of Neural Engineering., vol. 11, No. 3, p. 035009, 2014.

Simone Vossel et al., "Dorsal and ventral attention systems distinct neural circuits but collaborative roles," Neuroscientist, vol. 20, No. 2, pp. 150-159, 2014.

G. Pfurtscheller et al., "Event-related EEG/MEG synchronization and desynchronization: Basic principles," Clinicl Neurophysiology, vol. 110, No. 11, pp. 1842-1857, 1999.

Jianping LIU et al., "EEG-based estimation of mental fatigue by using KPCA-HMM and complexity parameters," Biomedical Signal Process and Control, vol. 5, No. 2, pp. 124-130, 2010.

Yongchang Li et al., "A real-time EEGbased BCI system for attention recognition in ubiquitous environment," in Proc. Int. Workshop Ubiquitous Affective Awareness Intell. Int., 2011, pp. 33-40.

Gert Pfurtscheller et al., "The hybrid BCI," Frontiers in Neuroscience, vol. 4, p. 3, Apr. 2010.

Andrew Myrden and Tom Chau, "A passive EEG-BCI for single-trial detection of changes in mental state," IEEE Transactions on Neural Systems and Rehabilitation Engineering, vol. 25, No. 4, pp. 345-356, Apr. 2017.

\* cited by examiner

EEG BRAIN-COMPUTER INTERFACE PLATFORM AND PROCESS FOR DETECTION OF CHANGES TO MENTAL STATE

FIELD

The present disclosure generally relates to the field of brain-computer interfaces.

INTRODUCTION

Embodiments described herein relate to brain-computer interfaces and electroencephalogram (EEG) devices. A brain-computer interface (BCI) is a communication pathway between a brain connected to electrodes and/or sensors, which are in turn connected to an external device. An EEG device detects electrical activity in brains using electrodes attached to portions of the head. Brain cells communicate via electrical impulses and are active all the time. This electrical activity can be detected and measured by an EEG recording.

SUMMARY

In accordance with an embodiment, there is provided a system for a brain-computer interface (BCI). The system comprises an output unit configured to trigger a series of mental tasks for the patient, a device having a plurality of electrodes to continuously capture real-time raw electroencephalography (EEG) data from a patient, a server, and a display device to display and update an interface with visual elements based on issued control commands from the server. The server has an acquisition unit configured to receive the electrode data, a processor configured to detect real-time changes in brain-state of the patient in response to the series of mental tasks for the patient, a presentation unit configured to generate visual elements for an interface in real-time, and a display controller configured to issue control commands to update the interface using the generated visual elements. The processor detects the real-time changes in brain-state using the electrode data. The processor is configured to generate a set of features based upon a frequency domain analysis of the EEG data, reduce the dimensionality of the set of features by implementing a feature clustering process to account for redundancy in EEG signal features of the EEG data, and classify the features into a mental state.

In some embodiments, the display device is part of a virtual reality headset.

In some embodiments, the visual elements are part of a train animation that moves in response to the real-time changes in brain-state of the patient.

In some embodiments, the visual elements are part of game that moves one or more features of a virtual character in response to the real-time changes in brain-state of the patient.

In some embodiments, the interface comprises a topographic map representing a plurality of portions of a brain of the patient, and the visual elements comprise an overlay of activated portions based on the real-time changes in brain-state of the patient.

In some embodiments, the device having the plurality of sensors or electrodes is an in-ear electroencephalography device having an over-ear support arm and an earpiece.

In some embodiments, the earpiece has two electrodes and the over-ear support arm has a reference electrode.

In some embodiments, the system further comprises a collector device coupled to the plurality of electrodes for pre-processing the real-time raw EEG data and correlating to the series of mental tasks on a common timeline.

In some embodiments, the output unit is configured to attempt to elicit a change in a mental state by a sequential trigger of the series of mental tasks based on a dynamic selection specific to the patient. Each mental task is selected from the set of an arithmetic task, an anagram task, and a grid-recall task. Each mental task is to be performed within a time period for that mental task. Each mental task type comprises at least two difficulty levels ranging from easy to difficult.

In some embodiments, the time period for each arithmetic task is 30 seconds, the time period for each anagram task is 20 seconds, and the time period for each grid-recall task is 15 seconds.

In some embodiments, the number of difficulty levels for each task type is five. The difficulty levels for each task type comprise very easy, easy, average, difficult and very difficult. The mental tasks are triggered in pseudo-random order with some clustering of very easy tasks and very difficult tasks.

In some embodiments, the visual elements represent the mental state of the patient displayed on the display device.

In some embodiments, the mental state of the patient is monitored via passive BCI monitoring in parallel with active BCI monitoring.

In some embodiments, where the output unit and the display device are the same device.

In some embodiments, the processor is further configured to oversample data collected at a more contemporaneous time, such that the data collected at the more contemporaneous time is weighted more heavily than historical data.

In some embodiments, to generate the set of features, the processor is further configured to compute a fast Fourier Transform (FFT) for each signal received from each electrode, resulting in a frequency spectrum, and compute a total spectral power within non-overlapping frequency ranges in the frequency spectra.

In some embodiments, the non-overlapping frequency ranges comprise a one Hz frequency range from zero-one Hz to 29-30 Hz.

In some embodiments, each spectral power measurement comprises a feature for classification.

In some embodiments, to reduce the dimensionality of the set of features, the processor is further configured to apply a clustering process to group the features from each electrode into data-sensitive frequency bands, and apply a fast correlation-based filter to select between two and 20 features for classification.

In some embodiments, wherein to classify the features into mental states, the processor is further configured to apply a shrinkage linear discrimination analysis to the frequency spectra data of selected features for classification, and determine the mental state based on the frequency ranges having higher spectral power.

In some embodiments, the mental state is one of fatigue when features originated from frontal and central electrodes, frustration when features originated from alpha band activity from posterior electrodes and other electrodes in the central and frontal regions, and attention when features originated from alpha band activity from posterior electrodes and not from other electrodes in the central and frontal regions.

In accordance with another embodiment, there is provided a method of detecting a mental state from multichannel EEG data continuously received from electrodes located relative to a patient. The method comprises, at a processor, generating a set of features based upon a frequency domain analysis of the EEG data, reducing the dimensionality of the set of features using a feature clustering process to account for redundancy in EEG signal features of the EEG data, classifying the features into a mental state, generating visual elements for an interface in real-time, and triggering the display of the visual elements for the interface on a display device. The visual elements represent the mental state of the patient.

In some embodiments, the method further comprises, at the processor, oversampling data collected at a more contemporaneous time, such that the data collected at the more contemporaneous time is weighted more heavily than historical data.

In some embodiments, the step of generating a set of features comprises computing a fast Fourier Transform (FFT) for each signal received from each electrode, resulting in a frequency spectrum, and computing a total spectral power within non-overlapping frequency ranges in the frequency spectra.

In some embodiments, the non-overlapping frequency ranges comprise a one Hz frequency range from zero-one Hz to 29-30 Hz.

In some embodiments, each spectral power measurement comprises a feature for classification.

In some embodiments, the step of reducing the dimensionality comprises applying a clustering process to group the features from each electrode into data-sensitive frequency bands, and applying a fast correlation-based filter to select between two and 20 features for classification.

In some embodiments, the step of classifying the features into the mental state comprises applying a shrinkage linear discrimination analysis to the frequency spectra data of selected features for classification, and determining the mental state based on the frequency ranges having higher spectral power.

In some embodiments, the mental state is one of fatigue when features originated from frontal and central electrodes, frustration when features originated from alpha band activity from posterior electrodes and other electrodes in the central and frontal regions, and attention when features originated from alpha band activity from posterior electrodes and not from other electrodes in the central and frontal regions.

In some embodiments, at a collector device, pre-processing the real-time electrode data and correlating to the series of mental tasks on a common timeline.

In accordance with another embodiment, there is provided a non-transitory computer-readable storage medium comprising computer-executable instructions for causing a processor to generate a set of features based upon a frequency domain analysis of the EEG data, reduce the dimensionality of the set of features using a feature clustering process to account for redundancy in EEG signal features of the EEG data, classify the features into a mental state, generate visual elements for an interface in real-time, and trigger the display of the visual elements for the interface on a display device. The visual elements representing the mental state of the patient.

In accordance with another embodiment, there is provided a processing device for real-time brain monitoring. The processing device comprises a network interface for acquisition of real-time raw EEG data for a patient's brain, a server for processing the real-time raw EEG data to compute real-time changes in brain state of the patient using feature clustering to account for redundancy in EEG signal features of the EEG data, a storage device for storing the real-time changes in brain state of the patient, and a display device having the interface to generate and update a visual representation of the real-time changes in brain state of the patient based on the issued control commands from the server.

In accordance with another embodiment, there is provided a system for a brain-computer interface (BCI). The system comprises a device having a plurality of electrodes to continuously capture real-time raw electroencephalography (EEG) data from a patient and a server. The server has an acquisition unit configured to receive the electrode data, a processor configured to detect real-time changes in brain-state of the patient in response to the series of mental tasks for the patient. The processor detects the real-time changes in brain-state using the electrode data. The processor is configured to generate a set of features based upon a frequency domain analysis of the EEG data, reduce the dimensionality of the set of features by implementing a feature clustering process to account for redundancy in EEG signal features of the EEG data, and classify the features into a mental state.

In some embodiments, the system further comprises a display device that is part of a virtual reality headset.

In some embodiments, the server further comprises a presentation unit to generate visual elements for an interface in real-time, and a display controller to issue control commands to update the interface using the generated visual elements. The visual elements represent real-time changes in brain-state of the patient. The visual elements are part of a train animation that moves in response to the real-time changes in brain-state of the patient.

In some embodiments, the visual elements are part of game that moves one or more features of a virtual character in response to the real-time changes in brain-state of the patient.

In some embodiments, the interface comprises a topographic map representing a plurality of portions of a brain of the patient. The visual elements comprise an overlay of activated portions based on the real-time changes in brain-state of the patient.

In some embodiments, the device having the plurality of sensors or electrodes is an in-ear electroencephalography device having an over-ear support arm and an earpiece.

In some embodiments, the earpiece has two electrodes and the over-ear support arm has a reference electrode.

In some embodiments, the system further comprises a collector device coupled to the plurality of electrodes for pre-processing the real-time raw EEG data and correlating to the series of mental tasks on a common timeline.

In some embodiments, the output unit is configured to attempt to elicit a change in a mental state by a sequential trigger of the series of mental tasks based on a dynamic selection specific to the patient. Each mental task is selected from the set of an arithmetic task, an anagram task, and a grid-recall task. Each mental task is to be performed within a time period for that mental task. Each mental task type comprises at least two difficulty levels ranging from easy to difficult.

In some embodiments, the time period for each arithmetic task is 30 seconds, the time period for each anagram task is 20 seconds, and the time period for each grid-recall task is 15 seconds.

In some embodiments, the number of difficulty levels for each task type is five. The difficulty levels for each task type comprise very easy, easy, average, difficult and very difficult. The mental tasks are triggered in pseudo-random order with some clustering of very easy tasks and very difficult tasks.

In some embodiments, the visual elements represent the mental state of the patient displayed on the display device.

In some embodiments, the mental state of the patient is monitored via passive BCI monitoring in parallel with active BCI monitoring.

In some embodiments, where the output unit and the display device are the same device.

In some embodiments, the processor is further configured to oversample data collected at a more contemporaneous time, such that the data collected at the more contemporaneous time is weighted more heavily than historical data.

In some embodiments, to generate the set of features, the processor is further configured to compute a fast Fourier Transform (FFT) for each signal received from each electrode, resulting in a frequency spectrum, and compute a total spectral power within non-overlapping frequency ranges in the frequency spectra.

In some embodiments, the non-overlapping frequency ranges comprise a one Hz frequency range from zero-one Hz to 29-30 Hz.

In some embodiments, each spectral power measurement comprises a feature for classification.

In some embodiments, to reduce the dimensionality of the set of features, the processor is further configured to apply a clustering process to group the features from each electrode into data-sensitive frequency bands, and apply a fast correlation-based filter to select between two and 20 features for classification.

In some embodiments, wherein to classify the features into mental states, the processor is further configured to apply a shrinkage linear discrimination analysis to the frequency spectra data of selected features for classification, and determine the mental state based on the frequency ranges having higher spectral power.

In some embodiments, the mental state is one of fatigue when features originated from frontal and central electrodes, frustration when features originated from alpha band activity from posterior electrodes and other electrodes in the central and frontal regions, and attention when features originated from alpha band activity from posterior electrodes and not from other electrodes in the central and frontal regions.

In accordance with another embodiment, there is provided a method of detecting a mental state from multichannel EEG data continuously received from electrodes located relative to a patient. The method comprises, at a processor, generating a set of features based upon a frequency domain analysis of the EEG data, reducing the dimensionality of the set of features using a feature clustering process to account for redundancy in EEG signal features of the EEG data, and classifying the features into a mental state.

In some embodiments, the method further comprises generating visual elements for an interface in real-time, and triggering the display of the visual elements for the interface on a display device. The visual elements represent the mental state of the patient.

In some embodiments, the method further comprises, at the processor, oversampling data collected at a more contemporaneous time, such that the data collected at the more contemporaneous time is weighted more heavily than historical data.

In some embodiments, the step of generating a set of features comprises computing a fast Fourier Transform (FFT) for each signal received from each electrode, resulting in a frequency spectrum, and computing a total spectral power within non-overlapping frequency ranges in the frequency spectra.

In some embodiments, the non-overlapping frequency ranges comprise a one Hz frequency range from zero-one Hz to 29-30 Hz.

In some embodiments, each spectral power measurement comprises a feature for classification.

In some embodiments, the step of reducing the dimensionality comprises applying a clustering process to group the features from each electrode into data-sensitive frequency bands, and applying a fast correlation-based filter to select between two and 20 features for classification.

In some embodiments, the step of classifying the features into the mental state comprises applying a shrinkage linear discrimination analysis to the frequency spectra data of selected features for classification, and determining the mental state based on the frequency ranges having higher spectral power.

In some embodiments, the mental state is one of fatigue when features originated from frontal and central electrodes, frustration when features originated from alpha band activity from posterior electrodes and other electrodes in the central and frontal regions, and attention when features originated from alpha band activity from posterior electrodes and not from other electrodes in the central and frontal regions.

In some embodiments, at a collector device, pre-processing the real-time electrode data and correlating to the series of mental tasks on a common timeline.

In accordance with another embodiment, there is provided a non-transitory computer-readable storage medium comprising computer-executable instructions for causing a processor to generate a set of features based upon a frequency domain analysis of the EEG data, reduce the dimensionality of the set of features using a feature clustering process to account for redundancy in EEG signal features of the EEG data, and classify the features into a mental state.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures.

It is understood that throughout the description and figures, like features are identified by like reference numerals.

DETAILED DESCRIPTION

Embodiments of methods, systems, and apparatus are described through reference to the drawings.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

Traditional brain-computer interfaces often exhibit unstable performance over time. Passive brain-computer interfaces may provide a way to complement and stabilize these traditional systems. Embodiments described herein can provide a passive brain-computer interface that uses electroencephalography to monitor changes in mental state on a single-trial basis. An example experiment recorded cortical activity from 15 locations while 11 able-bodied adults completed a series of challenging mental tasks. Using a feature clustering process to account for redundancy in EEG signal features, embodiments classified self-reported changes in fatigue, frustration, and attention levels with 74.8±9.1%, 71.6±5.6%, and 84.8±7.4% accuracy, respectively. Based on the most frequently-selected features across all participants, embodiments can have frontal and central electrodes for fatigue detection, posterior alpha band and frontal beta band activity for frustration detection, and posterior alpha band activity for attention detection. In some embodiments, these results can be integrated with an active brain-computer interface.

Figure 1:
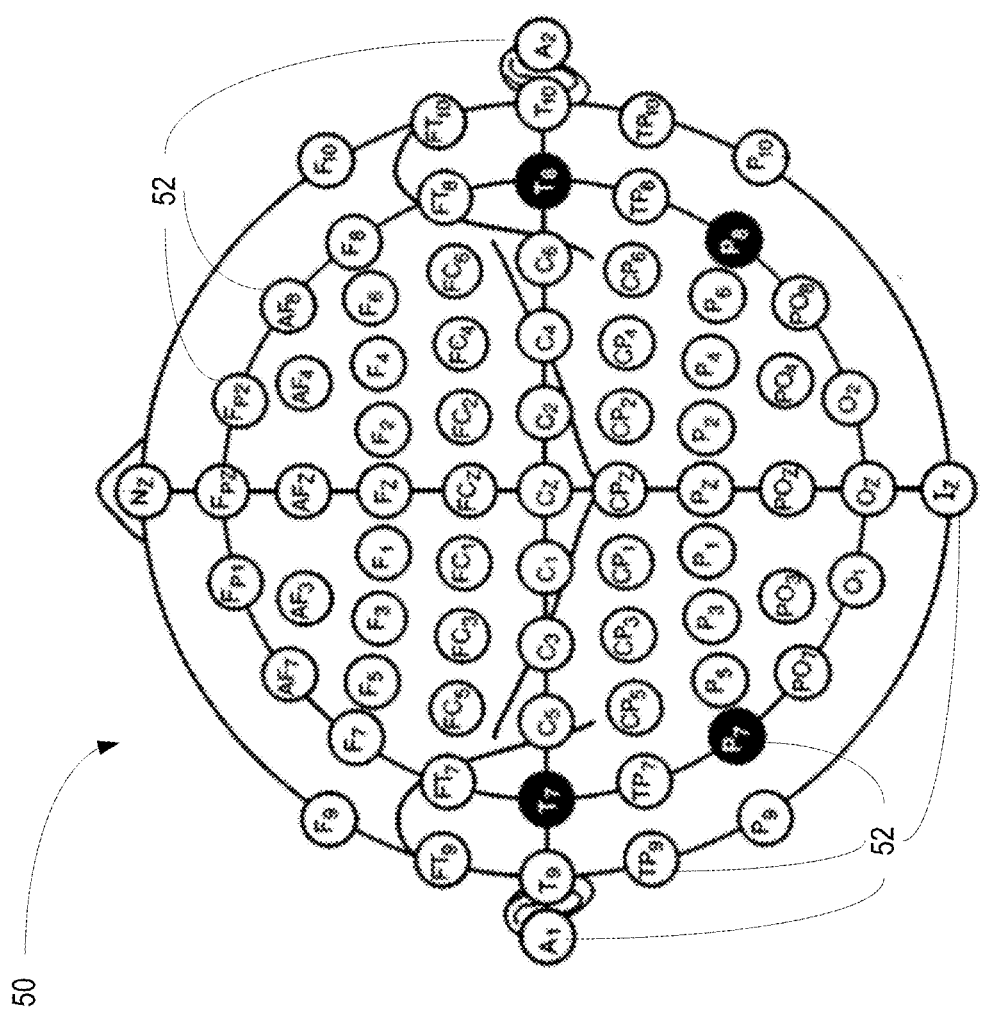
FIG. 1 illustrates an example of an EEG 10-20 system.

FIG. 1 illustrates an example of an EEG 10-20 system 50. The figure shows electrode 52 placement and nomenclature as standardized by the American Electroencephalographic Society.

Figure 2:
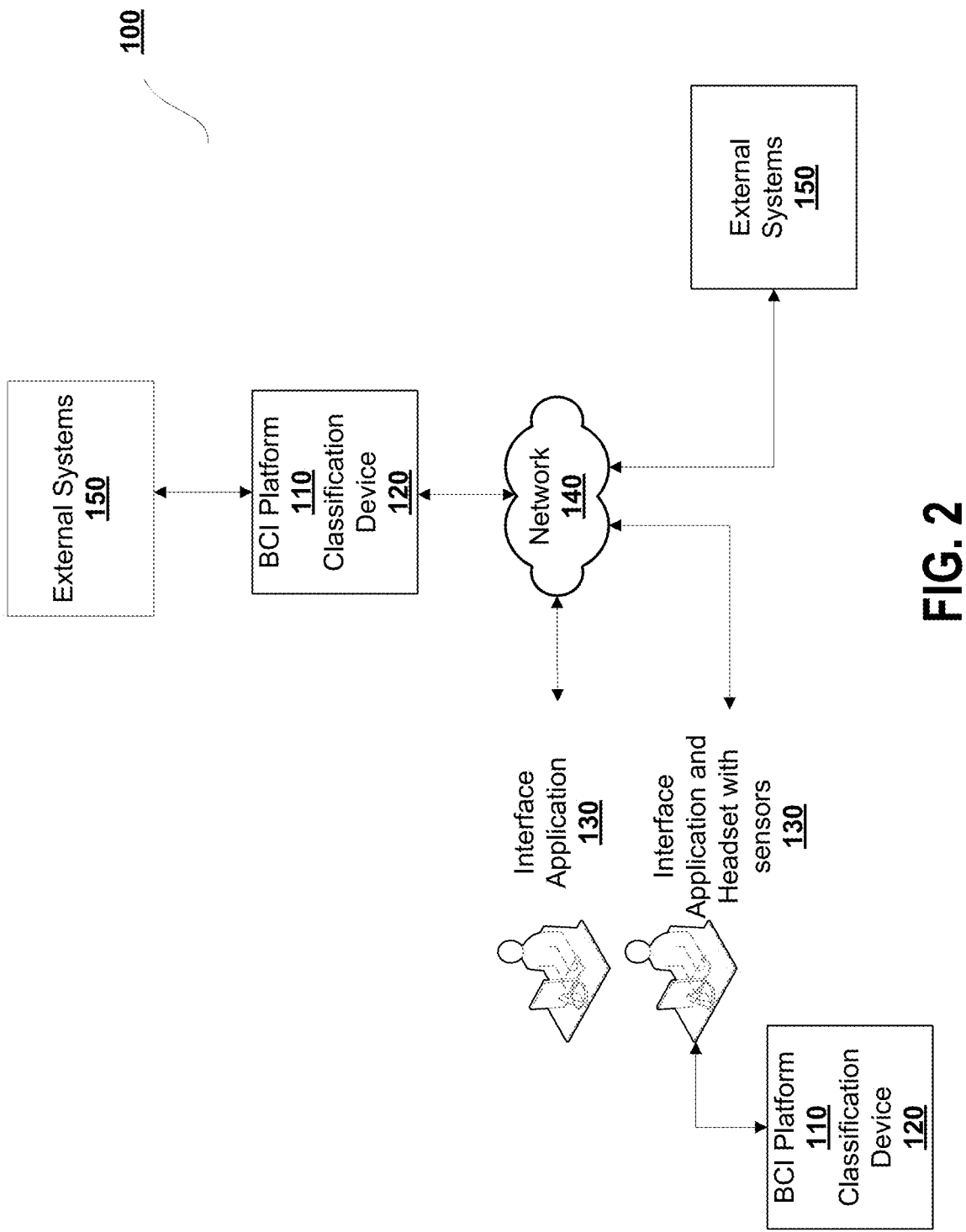
FIG. 2 is a view of an example brain-computer interface platform and interface application, in accordance with some embodiments.

FIG. 2 is a view of an example brain-computer interface (BCI) system 100, in accordance with some embodiments. BCI system 100 includes BCI platform 110, which includes classification device 120. BCI platform 110 connects to interface application 130, for example, to gather EEG data or other data from a user engaged with interface application 130. The data gathered or a modification of the data gathered may encode communication or input (such as EEG signals or other readings denoting brain activity) from individuals who are performing mental tasks. The interface application 130 can include electrodes to generate EEG signals. Interface application 130 can include other sensors, for example. Interface application 130 and BCI platform 110 can receive other types of data, including imaging data, for example. Interface application 130 can include one or more clocks to synchronize data collected from different sensors and modalities.

BCI platform 110 can connect to interface application 130 to cause one or more questions or stimuli to be presented to a user engaged at interface application 130, and to receive one or more responses to stimuli or other data input from the user. The stimuli can be presented on a display device using an interface generated by interface application 130. The stimuli can be presented by way of an audio signal and speaker, as another example. BCI platform 110 can organize the received data or aggregate the data with other data. For example, data from a stimulus can be used by BCI platform 110 to verify collected EEG data encoding the user's mental state. BCI platform 110 can organize the received data or aggregate the data with other data using time stamps and clock data for synchronization.

Interface application 130 can engage a user, for example, via electrodes 52 strategically placed on the user's scalp corresponding to brain regions providing discriminative information or showing activation, such as data corresponding to mental state. In some embodiments, the electrodes 52 may form part of a headset that is engaged with a BCI platform 110, or houses a BCI platform 110. The headset can additionally process data. Interface application 130 can also engage a user via a display, interactive display, keyboard, mouse, or other sensory apparatus. Interface application 130 can transmit and receive signals or data from such devices and cause data to be sent to BCI platform 110.

In some embodiments, the headset may be an in-ear EEG device monitoring a subset of the electrodes 52. An example of an in-ear EEG device is described in U.S. application No. 62/615,108, titled "In-Ear EEG Device and Brain-Computer Interfaces" and filed Jan. 9, 2018, which is hereby incorporated by reference herein in its entirety.

In some embodiments, interface application 130 can process data before sending the data via network 140 and/or to BCI platform 110. A user can be engaged with interface application 130 via electrodes 52 or a headset. In some embodiments, BCI platform 110 and/or classification device 120 can be housed in the headset or other means of engagement with interface application 130. In some embodiments, BCI platform 110 and/or classification device 120 can connect to interface application 130 over a network 140 (or multiple networks).

Classification device 120 associated with BCI platform 110 can receive sensor data, for example, EEG data from a single user via interface application 130. Classification device 120 can receive stored data from one or more external systems 150 or interface applications 130, such as data corresponding to other sessions of data collection, for example. Classification device 120 can build or train a classification model using this data, for example, EEG data from a single user. Classification device 120 can use the classifier to classify mental states of the user and cause a result to be sent to an entity 150 or interface application 130. The result can cause an entity to actuate a response, which can be feedback to the user, an alert to a caregiver, or data for a researcher.

The classifier can be re-trained on additional EEG data, for example, data collected from the user at a more contemporaneous time. This may improve the accuracy of the classifier, for example, if same session data are more relevant than data collected from previous days. Further, additional data may improve the accuracy of the classifier so it can be continuously updated and trained as more data and feedback is provided to the BCI platform 110.

BCI platform 110 can connect to interface application 130 via a network 140 (or multiple networks). Network 140 (or multiple networks) is capable of carrying data and can involve wired connections, wireless connections, or a combination thereof. Network 140 may involve different network communication technologies, standards and protocols, for example.

In some embodiments, external systems 150 can connect to BCI platform 110 and/or classification device 120, for example, via network 140 (or multiple networks). External systems 150 can be one or more databases or data sources or one or more entities that aggregate or process data. For example, an external system 150 can be a second BCI platform 110 that collects EEG data (or other data), performs feature extraction on the data, and builds a classification model. The external system 150 can then process the data and/or build one or more classification models based on a selection of features. The one or more classification models can be used by one or more other BCI platforms 110, stored in a database, and/or transmitted to an external system 150, for example, that is accessible by researchers or developers.

External systems 150 can receive data from an interface application 130, BCI platform 110, and/or classification device 120. This data can include raw data collected by interface application 130, such as EEG data from electrodes 52 placed on a user's scalp, data processed by interface application 130, BCI platform 110, and/or classification device 120 (including a classification device 120 housed in a headset associated with electrodes 52 placed on a user's scalp), and/or data from one or more other external systems 150. This connectivity can facilitate the viewing, manipulation, and/or analysis of the data by a researcher, developer, and/or healthcare provider engaged with an external system 150.

Figure 3:
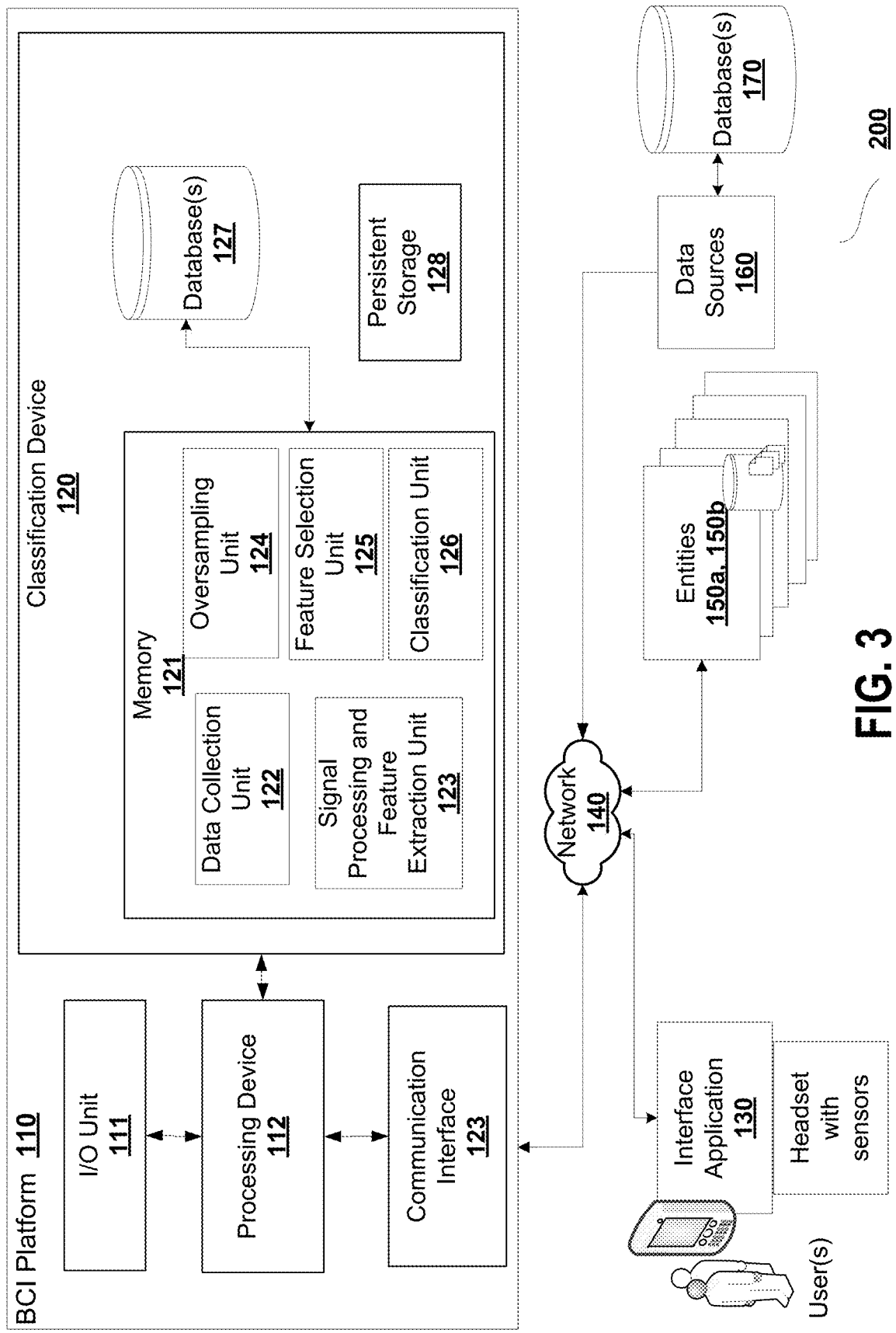
FIG. 3 is a view of an example BCI platform and classification device, in accordance with some embodiments.

FIG. 3 is a view of an example BCI platform 110 and classification device 120, in accordance with some embodiments. A BCI platform 110 can include an I/O unit 111, processing device 112, communication interface 123, and classification device 120.

A BCI platform 110 can connect with one or more interface applications 130, entities 150, data sources 160, and/or databases 170. This connection may be over a network 140 (or multiple networks). BCI platform 110 receives and transmits data from one or more of these via I/O unit 111. When data is received, I/O unit 111 transmits the data to processing device 112.

Each I/O unit 111 can enable the BCI platform 110 to interconnect with one or more input devices, such as a keyboard, mouse, camera, touch screen and a microphone, and/or with one or more output devices such as a display screen and a speaker.

A processing device 112 can execute instructions in memory 121 to configure classification device 120, and more particularly, data collection unit 122, signal processing and feature extraction unit 123, oversampling unit 124, feature selection unit 125, and classification unit 126. A processing device 112 can be, for example, any type of general-purpose microprocessor or microcontroller, a digital signal processing (DSP) processor, an integrated circuit, a field programmable gate array (FPGA), a reconfigurable processor, or any combination thereof. The oversampling is optional and in some embodiments there may not be an oversampling unit.

Memory 121 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Storage devices 120 can include memory 121, databases 127, and persistent storage 128.

Each communication interface 123 can enable the BCI platform 110 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The BCI platform 110 can be operable to register and authenticate users (using a login, unique identifier, and password for example) prior to providing access to applications, a local network, network resources, other networks and network security devices. The platform 110 may serve one user or multiple users.

The storage 127 may be configured to store information associated with or created by the classification device 120. Storage 127 and/or persistent storage 128 may be provided using various types of storage technologies, such as solid-state drives, hard disk drives, flash memory, and may be stored in various formats, such as relational databases, non-relational databases, flat files, spreadsheets, extended markup files, etc.

Classification device 120 can be used to build a classification model by training on data received from interface application 130 or other entities 150, for example, EEG data collected during a change in mental state of a user. Data collection unit 122 associated with a classification device 120 and BCI platform 110 can receive data, for example, EEG data from a single user via interface application 130. Data collection unit 122 can receive stored data from one or more external systems 150 or interface applications 130, for example, corresponding to other sessions of data collection.

Signal processing and feature extraction unit 123 associated with a classification device 120 can process the data or EEG signals, for example, to remove linear trends, electrical noise, and EEG artifacts, and can reconstruct the EEG signal from the remaining components.

Signal processing and feature extraction unit 123 can extract features from the data or EEG data using one or more feature extraction methods, such as common spatial pattern, matched-filtering, spectral power estimates, or auto-regressive (Yule-Walker) model of order of magnitude, e.g., three, or wavelet transform. This can produce a vector of features. The dimensionality of the feature vector can vary.

Oversampling unit 124 can sample the data or EEG data, for example, to oversample data collected at a more contemporaneous time. In some embodiments, cost-sensitive classification can be used to give the more contemporaneous data larger coefficients in the cost function compared to data collected on, for example, a previous day. Oversampling unit 124 can thus facilitate higher classification accuracies, for example, by oversampling data collected from the same session that the classification model once built will be used to classify EEG data from. The oversampling is optional, and in some embodiments there may not be an oversampling step.

Feature selection unit 125 can select features from the features extracted from the data or EEG data. This may help reduce or avoid overfitting the data, facilitate the generalizability of the data, or facilitate the applicability of a classifier modelled on the data or features extracted from the data. In some embodiments, a classification model is trained on data or features selected from a single user, for example, the ten best features extracted from a set of features extracted from the data collected from the user. The features may be selected based on how they relate to accuracy of the resulting classification model or lowest error.

Classification unit 126 associated with the classification device 120 can use the selected features to train an algorithm, such as a linear support vector machine. The algorithm can be used for machine learning classification of data to facilitate classification of mental state given EEG data as input. For example, BCI platform 110 can use EEG data to build a support vector machine classification model for a particular user who was or is engaged with interface application 130. The classifier can be re-trained on additional EEG data, for example, data collected from the user at a more contemporaneous time. This may improve the accuracy of the classifier, for example, if same session data are more valuable than data collect from previous days.

At a later time or at a time immediately following re-training of the classifier, interface application 130 can receive EEG data from the user, for example, corresponding to the user's mental state. Interface application 130 can transmit the data to BCI platform 110. As described above, data collection unit 122 can collect the EEG data, signal processing and feature extraction unit 123 can process the data and extract features, feature selection unit 125 can select the relevant subset of features, and classification unit 126 can use the personalized classification model for that user to help determine the user's mental state. An example classification model can be a support vector machine classification model. Another example classification model can be a shrinkage linear discriminant analysis model. The determination can be processed and/or presented to a user via interface application 130 or transmitted to an external system 150, for example, a device or system accessible by a caregiver or researcher.

Figure 4:
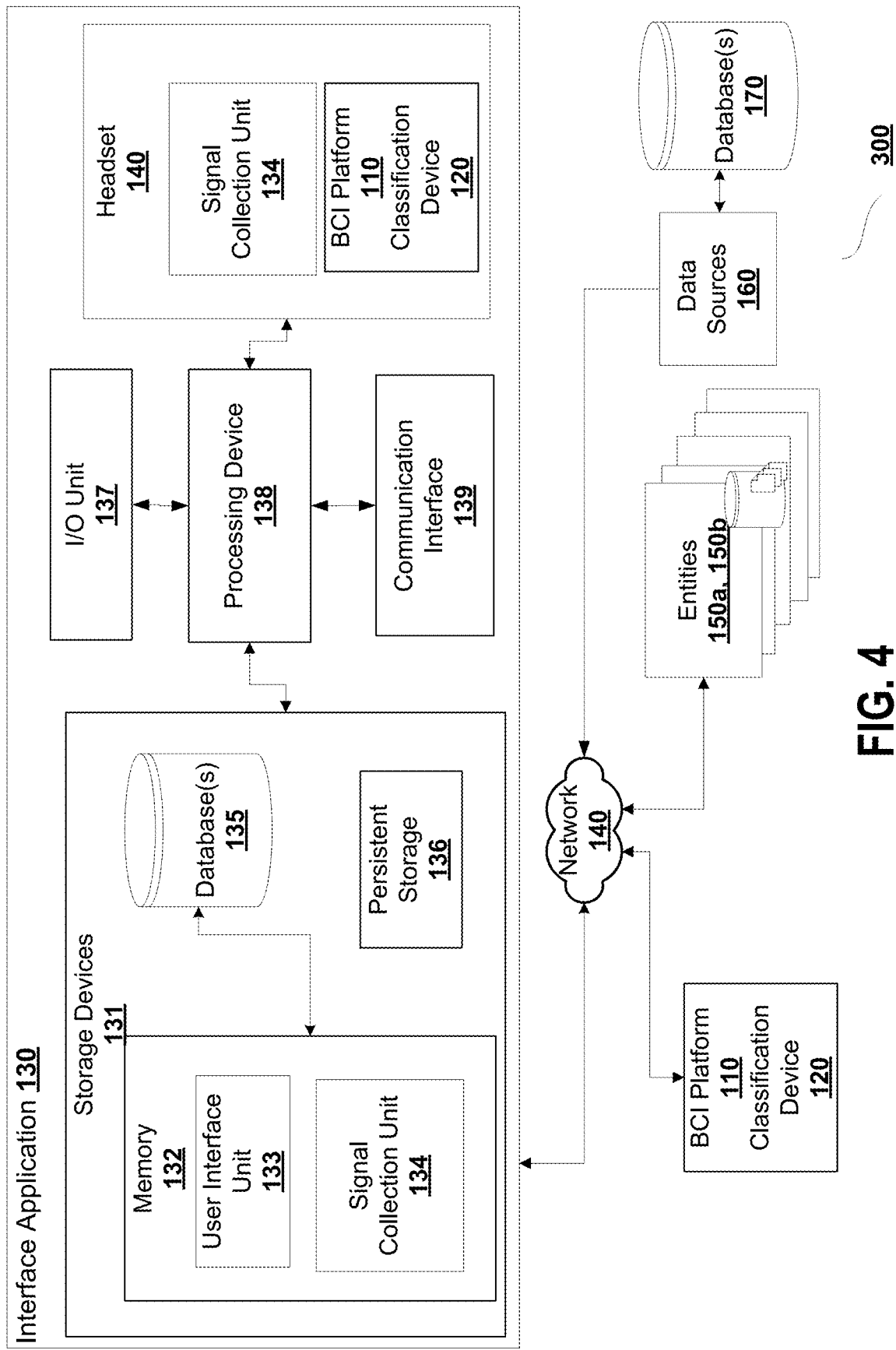
FIG. 4 is a view of an example interface application, in accordance with some embodiments.

FIG. 4 is a view of an example interface application 130. In some embodiments, interface application 130 includes a classification device 120. In some embodiments, interface application 130 is connected to a headset associated with or housing a BCI platform 110 and classification device 120. The headset may include multiple electrodes 52 to collect EEG data when connected to a user's scalp. In some embodiments, the headset may comprise an in-ear EEG device as described in U.S. application No. 62/615,108, titled "In-Ear EEG Device and Brain-Computer Interfaces" and filed Jan. 9, 2018, which is incorporated herein by reference. The signals may be collected by signal collection unit 134, which may connect to BCI platform 110 housed within the headset. The BCI platform 110 can create and/or use one or more classifiers as described above. For example, the BCI platform 110 within a headset 140 can train and retrain a classifier using EEG data from one or more sessions from a single user engaged with interface application 130 or headset 140. BCI platform 110 can use the classifier to classify mental states of the user using further EEG signals. BCI platform 110 may be operable as described above.

In some embodiments, signal collection unit 134 may be associated with an interface application 130 that does not include a headset 140. Signal collection unit 134 can gather data, for example EEG data, from a user engaged with interface application 130. Interface application 130 can then cause transmission of data, the EEG signals, processed data or processed EEG signals, or other information to a BCI platform 110 and/or classification device 120 over a network 140 (or multiple networks). The BCI platform 110 can train and retrain a classifier using EEG data from one or more sessions from a single user engaged with interface application 130 or headset 140. BCI platform 110 can use the classifier to classify mental states of the user using further EEG signals. BCI platform 110 may be operable as described above.

In some embodiments, interface application 130 connects to a BCI platform 110 and classification device 120 over a network 140 (or multiple networks).

Each I/O unit 311 enables the interface application 130 (including headset 140) to interconnect with one or more input devices, such as a keyboard, mouse, camera, touch screen, microphone, electrodes, headset, or other sensory collection devices, for example, that can detect brain activity or mental state. Each I/O unit 311 also enables the interface application 130 (including headset 140) to interconnect with one or more output devices such as a display screen, speaker, or other devices presenting visuals, haptics, or audio.

A processing device 138 can execute instructions in memory 132 to configure user interface unit 133 and signal collection unit 134. A processing device 138 can be, for example, any type of general-purpose microprocessor or microcontroller, a digital signal processing (DSP) processor, an integrated circuit, a field programmable gate array (FPGA), a reconfigurable processor, or any combination thereof.

Memory 132 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Storage devices 131 can include memory 132, databases 135, and persistent storage 136.

Each communication interface 139 can enable the interface application 130 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

The interface application 130 can be operable to register and authenticate users (using a login, unique identifier, and password for example) prior to providing access to applications, a local network, network resources, other networks and network security devices. The platform 110 may serve one user or multiple users.

The database 135 may be configured to store information associated with or created by the classification device 120. Database 135 and/or persistent storage 136 may be provided using various types of storage technologies, such as solid-state drives, hard disk drives, flash memory, and may be stored in various formats, such as relational databases, non-relational databases, flat files, spreadsheets, extended markup files, and so on.

User interface unit 133 can manage the dynamic presentation, receipt, and manipulation of data, such as for example, input received from interface application 130. User interface unit 133 can associate the brain activity of the user, for example, gathered by a signal collection unit 134 and classified by a BCI platform 110, as a mental state and cause storage of same in storage devices 131 or transmission of same over network 140 (or multiple networks). As another example, user interface unit 133 can facilitate validation of a user mental state with the result determined by a BCI platform 110 or classifier. The interface application 130 can gather the mental state via I/O unit 137 connected to a keyboard, touchscreen, mouse, microphone, or other sensory device. User interface unit 133 can associate the brain activity with the mental state determined by a BCI platform 110 or classifier to verify the accuracy of the BCI platform 110 or classifier. In some embodiments, interface application 130 can transmit the response to a BCI platform 110.

Brain-computer interfaces (BCIs) have traditionally been defined as systems that allow control of an external device using thoughts alone. Potential applications for these devices have been identified within a diverse array of fields, including access technologies for physically impaired individuals, motor recovery, and entertainment. Conceptually, BCIs include three components: a measurement modality that monitors some physiological variable related to cognitive activity, a decoding module that translates this signal into a prediction of user intent, and an activation module that produces the desired output (e.g., a simulated key press or mouse click).

Existing BCIs use a variety of measurement modalities, including both invasive and non-invasive techniques. Invasive techniques, such as electrocorticography (ECoG) and single-cell recordings, require the implantation of electrodes within the brain. Non-invasive techniques, such as electroencephalography (EEG), near-infrared spectroscopy (NIRS), and transcranial Doppler (TCD) ultrasound, can be safely recorded from the surface of the skull. Most of these BCIs recognize and react to a specific voluntary cognitive activity. Example cognitive activities for BCI applications include the modulation of visuospatial attention (e.g., the P300 response), the performance of covert mental tasks (e.g., motor imagery), and the control of slow cortical potentials.

An alternative to this standard BCI paradigm has been proposed. By focusing on voluntary cognitive activity, existing BCIs discard a wealth of information regarding the underlying mental state of the BCI user. This information may include fatigue, attention, mental workload, and affective state. In some embodiments, more complex aspects of user state, such as perceived loss of control over a system, may be detectable. BCIs that focus on detecting and quantifying these underlying variables have been defined as passive BCIs. A diverse set of potential applications is proposed for these devices, including cognitive state monitoring and physiological computing. In some embodiments, passive BCIs may also be useful as supplements to traditional active BCIs, providing information about the underlying user state to facilitate greater accuracy in the classification of voluntary cognitive activity. This may be viewed as a type of context-awareness.

Previous active BCI studies have noted the apparent effects of some of these mental states on BCI performance. For example, users experiencing cognitive fatigue often struggle to complete the mental tasks required for BCI control. This may lead to deterioration in classification accuracy. Similarly, users experiencing frustration or distraction may have more difficulty controlling a BCI—the former because the physiological changes related to frustration inhibit concentration and the latter because it diverts attention from BCI operation.

It is desirable to design an active BCI that adapts to these changes to avoid compromised performance, provided that these changes can be detected with high accuracy. This adaptation could include modification of the learning algorithm itself or simply identification of an optimal range of mental states for BCI operation.

Several recent studies have investigated the detection of these mental states. For example, EEG-based fatigue detection has been the subject of both long-term sleep deprivation studies and shorter-duration studies that focus on mental task performance. Of these, the latter are more relevant to BCI applications. These studies have indicated that changes in fatigue levels can manifest as changes in spectral activity within each of the four major EEG frequency bands: delta, theta, alpha, and beta. Single-trial detection of these changes may result in classification accuracies approaching 90%, although such studies have often relied on sleep deprivation protocols that may not generalize to BCI usage. On the other hand, fewer studies have focused on EEG-based detection of attention, and those that exist have achieved classification accuracies no higher than 75%. Automatic detection of frustration, meanwhile, has received little attention in previous research.

In some embodiments, a protocol may be used in a study investigating changes in fatigue, frustration, and attention that may occur during the performance of three active mental tasks—mental arithmetic, anagram solution, and a short-term spatial memory task—and a rest task. As is described further below, changes in each state may be detected on a single-trial basis using EEG recordings. Furthermore, using a variety of mental tasks may allow an algorithm to identify the changes in EEG that reflect fluctuations in underlying mental state, not simply those related to the performance of particular tasks.

In one embodiment of a study, eleven participants (eight female, mean age 25±3.6 years) were recruited for one study. In this embodiment, participants had have no history of brain injury, were fluent in English, and refrained from consuming caffeine for four hours prior to the experiment. In this embodiment, all participants were right-handed. It is understood that in other embodiments, a different number of participants in different demographic categories may be recruited.

In the embodiment, each participant completed four one-hour sessions on separate days. Within each session, participants performed a series of 80 trials, divided into four blocks of 20 trials each. During each trial, participants performed one of four mental tasks: mental arithmetic, anagram solution, a grid-recall (short-term memory) task, and rest. It is understood that in other embodiments, a different number of sessions lasting a different duration of time may be completed by the participants. It is also understood that a different number of trials divided into a different number of blocks may be performed. It is also understood that different mental tasks may be performed to study different areas of the brain.

In the embodiment, during the mental arithmetic task, participants were prompted to complete an on-screen mathematical problem. Each problem involved a series of additions and/or subtractions with four operands. During the anagram task, participants were presented with a set of jumbled letters with only one English solution and prompted to enter the unscrambled word. During the grid-recall task, participants were presented with a five-by-five grid of squares. A pattern was highlighted on the grid by marking a subset of the squares red while leaving the remainder white. Participants were given five seconds to memorize the grid pattern, and, after a ten second break during which the grid was removed from the screen, were asked to recreate the initial pattern by manually highlighting squares on a blank grid. During the rest task, participants were simply instructed to relax and let their minds wander, mimicking the typical no-control state for BCI usage. Time limits were 30 seconds for mental arithmetic, 20 seconds for anagram solution, and 15 seconds for the grid recall task. It is understood that different types of mathematical, anagram and grid-recall tasks may be performed for the study.

Figure 5:
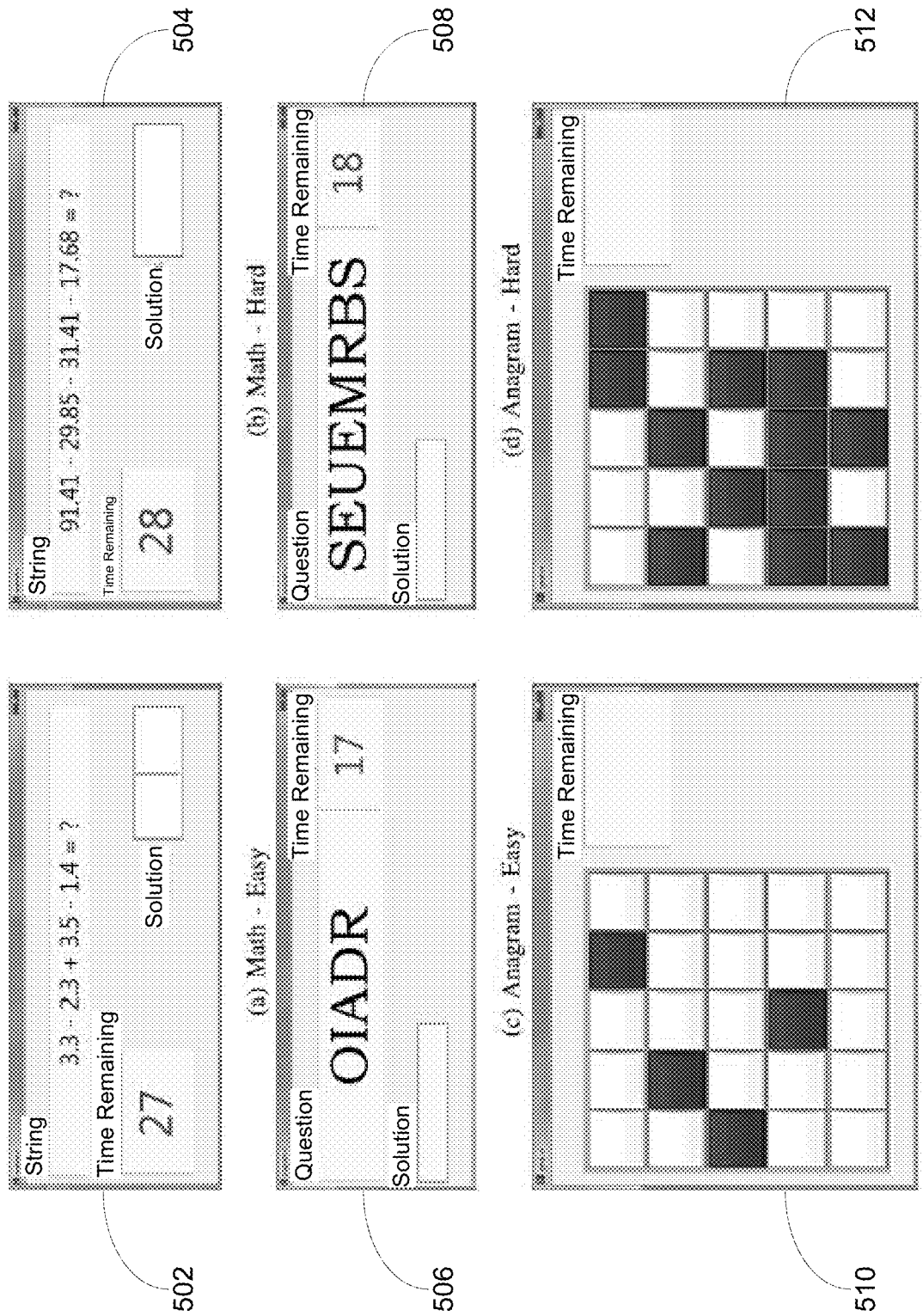
FIG. 5 illustrates, in screenshots, examples of easy and difficult cases for each active task, in accordance with some embodiments.

FIG. 5 illustrates, in screenshots, examples of easy and difficult cases for each active (i.e., non-rest) task, in accordance with some embodiments. FIG. 5 depicts two examples of each task: one classified as easy and one classified as hard (i.e., difficult). Examples of a math-easy task 502, a math-hard task 504, an anagram-easy task 506, an anagram-hard task 508, a grid-recall-easy task 510 and a grid-recall-hard task 512 are shown. In some embodiments, a short pilot study may be conducted to ensure that the assigned difficulty levels match the experienced difficulty levels.

In the embodiment, there were five difficulty levels for each non-rest (i.e., active) task, ranging from very easy to very hard/impossible. For the mental arithmetic task, difficulty was controlled by increasing the magnitude of, and the number of, significant digits in the operands. For the anagram task, difficulty was controlled by increasing the number of letters (ranging between 5 and 8) in the scrambled word, and, for the highest level, providing a set of letters that did not have a solution. For the grid-recall task, difficulty was controlled by increasing the number of highlighted squares, thereby increasing the complexity of the pattern to be memorized. It is understood that a different number of difficulty levels, and different tasks corresponding to those levels, may be used in the study.

In the embodiment, there were an equal number of trials at each difficulty level for each task. Trials were presented in a pseudo-random order, with some intentional clustering of both easy and difficult trials. These sustained intervals during which all trials were of trivial or extreme difficulty were intended to cause peaks and troughs in each mental state over time. During each non-rest trial, participants attempted to enter the correct answer before the time limit expired. Participants were permitted to use both hands to enter answers. However, to minimize the effects of movement on the recorded EEG signals, participants were instructed to remain completely still until they were ready to enter a final answer. It was not possible to completely avoid movement, as manual entry of answers was used to allow on-screen performance tracking. The direct feedback provided by this on-screen performance tracking was used to motivate participants and also to induce changes in frustration when performance was poor.

In the embodiment, after each trial, participants were prompted to self-report their perceived levels of fatigue, frustration, and attention. A five-point Likert scale may be used for each measure. The perceived difficulty of each trial was also self-reported on a five point scale. Participants completed the expanded Positive and Negative Effect Schedule (PANAS-X) prior to and at the conclusion of each session. It is understood that other and different scales and schedules may be used participants when self-reporting during a study.

Figure 6:
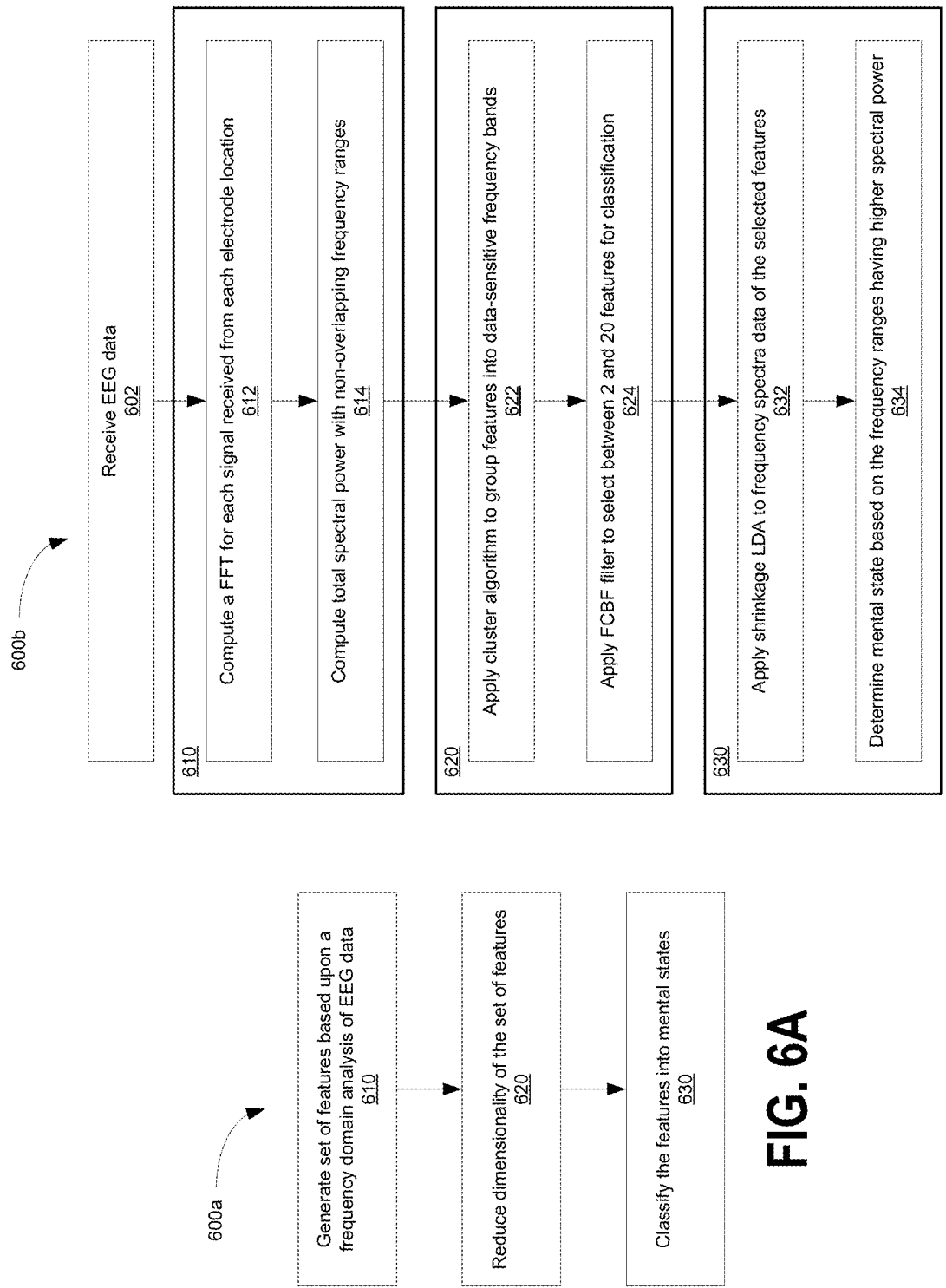
FIG. 6A illustrates, in a flowchart, an example of a method of determining a mental state from multichannel EEG data, in accordance with some embodiments.
FIG. 6B illustrates, in a flowchart, another example of a method of determining a mental state from multichannel EEG data, in accordance with some embodiments.

FIG. 6A illustrates, in a flowchart, an example of a method 600a of determining a mental state from multichannel EEG data, in accordance with some embodiments. The EEG data may be received from electrodes 52 located on a head of a patient, on an EEG cap device or on an in-ear EEG device. The method 600a may be performed by the BCI platform 110, classification device 120, and the interface application 130. The method 600a comprises generating 610 a set of features based upon a frequency domain analysis of the EEG data. Next, a dimensionality of the set of features is reduced 620. Next, the features are classified 630 into mental states. The method 600a will be described in more detail below.

FIG. 6B illustrates, in a flowchart, another example of a method 600b of determining a mental state from multichannel EEG data, in accordance with some embodiments. The EEG data may be received from electrodes 52 located on a head of a patient, on an EEG cap device or on an in-ear EEG device. The method 600b may be performed by the BCI platform 110, classification device 120, and the interface application 130. The method 600b includes receiving the EEG data 602. The step of generating 610 comprises computing 612 a fast Fourier Transform (FFT) for each signal received from each electrode location, and computing 614 total spectral power with non-overlapping frequency ranges. The step of reducing 620 comprises applying 622 a cluster algorithm to group features into data-sensitive frequency bands, and applying 624 a fast correlation-based filter (FCBF) to select between two and 20 features for classification. The step of classifying 630 comprises applying 632 a shrinkage linear discriminant analysis (LDA) to the frequency spectra data of the selected features, and determining 634 a mental state based on the frequency ranges having higher spectral power. Aspects of the method 600b will be described in more detail below.

In some embodiments, EEG data may be collected using a wireless B-Alert X24 headset. In one embodiment, signals were acquired from 15 electrodes 52 placed at the F3, F1, Fz, F2, F4, C3, C1, Cz, C2, C4, CPz, P1, Pz, P2, and POz cortical locations by the international 10-20 system. The international 10-20 system is shown in FIG. 1. The sampling rate was 256 Hz, and signal quality was monitored throughout the experiment. EEG signals may be acquired through a custom LabVIEW interface that also presented all required stimuli to participants.

In some embodiments, recorded EEG data may be filtered using a FIR band-pass filter (1-30 Hz) to isolate the frequencies of interest. The ADJUST algorithm for independent component analysis (ICA) may be used to remove eye movement and blink artefacts from the recorded signals. During the experiment, markers may be automatically inserted into the recorded EEG data at the beginning (i.e., the presentation of the task stimuli) and the end (i.e., the expiration of the time limit) of each trial. These markers may later be used to extract each trial from the recorded data for further analysis.

In some embodiments, a set of signal features may be constructed for each trial. These features may be based on frequency-domain analysis of the recorded EEG data. A fast Fourier Transform (FFT) may be computed for the EEG signal from every electrode location for each trial. The resultant frequency spectra may be used to compute the total spectral power within each non-overlapping 1 Hz frequency range from 0-1 Hz to 29-30 Hz. Each of these spectral power measurements may be used as a feature for classification. In one embodiment, for each trial, there were a total of 450 features (30 different frequencies from 15 different electrodes).

In some embodiments, following feature extraction, a 10×10 (runs×folds) repeated cross-validation may be used to estimate the accuracy of mental state detection. The same initial feature set may be used for each mental state, but feature selection and classification may be performed independently for each state, resulting in the construction of a unique classifier for each mental state.

In some embodiments, two stages of dimensionality reduction may be performed. First, a participant-specific feature clustering algorithm may be used to group the features from each electrode into data-sensitive frequency bands. This algorithm uses inter-feature correlations to identify highly similar clusters of features and derives individualized frequency bands rather than using the traditional definitions of the delta, theta, alpha, and beta bands. The 30 original frequency-domain features from each electrode 52 may be compressed into four to seven features per electrode 52, each of which represents the mean of a set of original features. Secondly, a fast correlation-based filter (FCBF) may be used to select between two and 20 features for classification. This maximum feature set dimensionality may be selected based on the number of samples (roughly 160 per class), and, in some embodiments, a recommendation to use no more than one feature for every five to ten training samples per class.

Due to the subjective and self-reported nature of the class labels, most participants may have levels of class imbalance (i.e., certain classes may have many more samples than others). In the most extreme cases, some participants may not self-report particular levels of a mental state (e.g., extremely high frustration) at any point during the experiment. To help mitigate this imbalance, each classification problem may be reduced to binary by collapsing the five-class representations of mental state.

Figure 7:
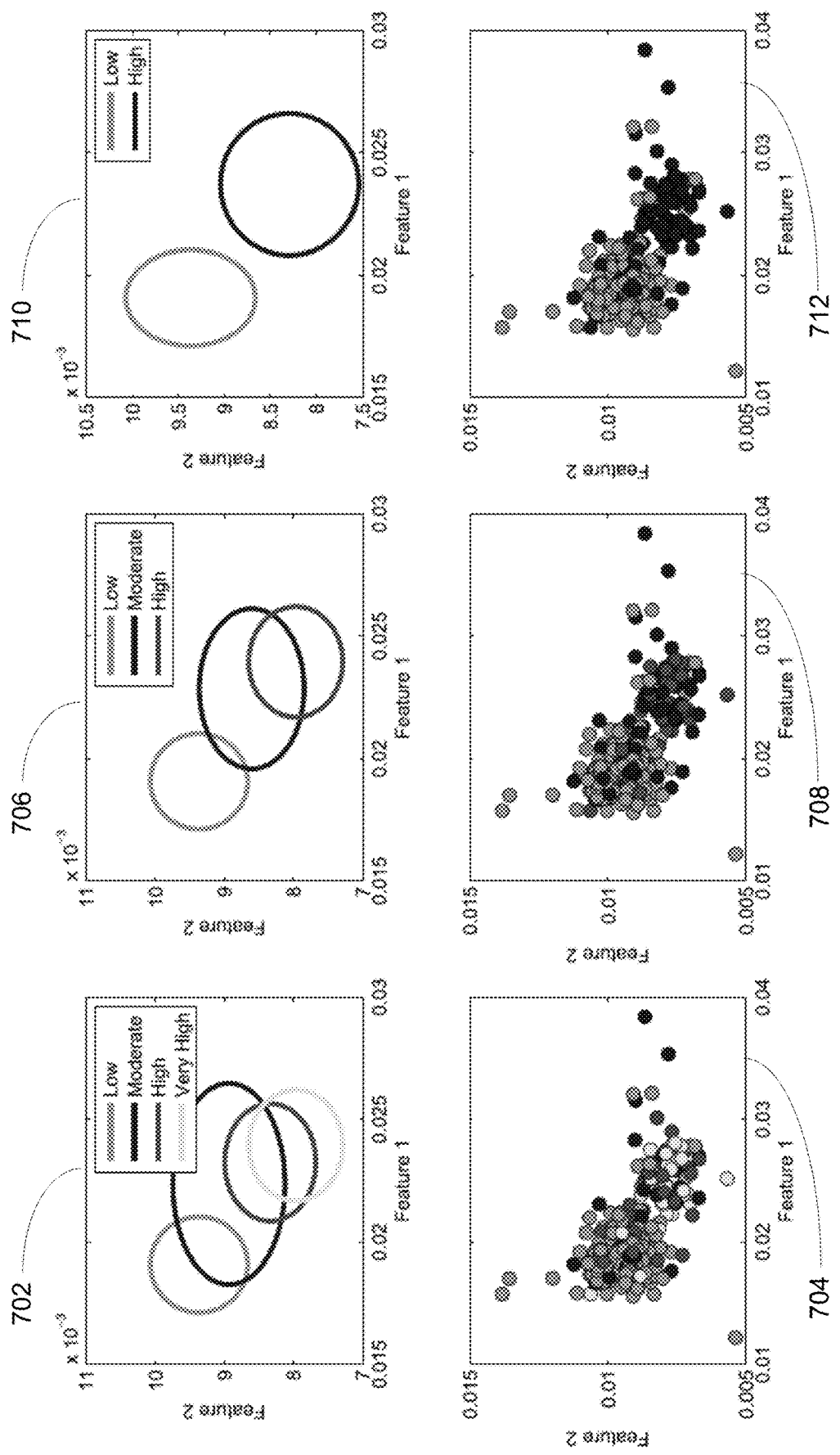
FIG. 7 illustrates, in graph diagrams, examples of iterative data relabeling for a participant's attention levels, in accordance with some embodiments.

During each fold of cross-validation, the number of classes may be reduced based on the training data alone. First, any extremely scarce classes (i.e., class frequency less than 10%, equivalent to half the average class frequency) may be identified. These classes may be combined with the nearest adjacent class (i.e., a class with self-reported level either one higher or lower), with the inter-class proximity determined by the Euclidean distance between the mean feature vector for each class. Second, the inter-class Euclidean distance may be computed for each remaining pair of adjacent classes, and the closest pair may be combined into one class. This procedure may continue iteratively until only two classes remain. FIG. 7 illustrates, in graph diagrams, examples of iterative data relabeling for a participant's attention levels, in accordance with some embodiments. The top row (graphs 702, 706, 710) displays only the class distributions while the bottom row (graphs 704, 708, 712) shows all data. Nearby classes are iteratively merged until only two classes remain. The final graph is prior to the removal of outlying data points and resampling. The class transformations resulting from this algorithm may then be applied to the testing data. The majority class within the training data may then be randomly under-sampled to generate a balanced set of training data.

In some embodiments, three different classifiers may be investigated: shrinkage linear discriminant analysis (LDA), support vector machines (SVM), and Gaussian naive Bayes (NB). For the SVM classifier, a radial basis function kernel may be used. Values may be set for a and the regularization constant C using a grid search over relevant values of each parameter ($2^2 \leq \sigma \leq 2^4$, $2^{-3} \leq C \leq 2^{-1}$) during an inner cross-validation on the training set. Target dimensionalities between two and 20 features may be used for all classifiers. Classifier performance may be measured using the balanced classification accuracy (i.e., the mean of sensitivity and specificity). The cortical areas and frequencies most often used for classification of each state may be identified.

Two alternative cases may be considered for practical reasons. In the first, smaller subsets of electrodes may be used for classification to investigate the feasibility of fatigue, frustration, and attention detection using less complex EEG headsets. In the second, the inter-participant generalizability of mental state detection may be investigated by performing feature selection for each participant based only on the remaining 10 participants, leaving classifier training as the only participant-dependent step in the classification algorithm.

Figure 8:
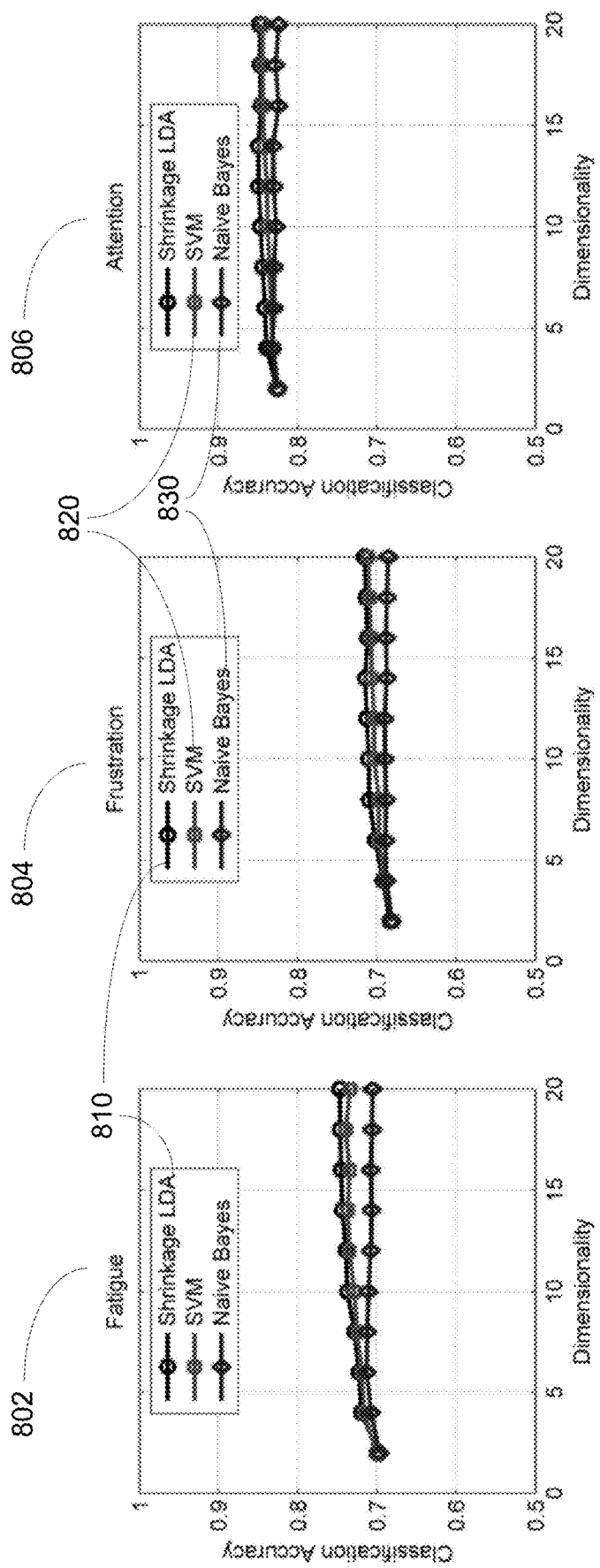
FIG. 8 illustrates, in graph diagrams, the relationship between number of features and balanced classification accuracy for each classifier, in accordance with some embodiments.

FIG. 8 illustrates, in graph diagrams, the relationship between number of features and balanced classification accuracy for each classifier, in accordance with some embodiments. FIG. 8. shows balanced classification accuracy for each mental state (fatigue 802, frustration 804 and attention 806) and classification algorithm for a range between two and 20 features. Shrinkage LDA is represented by line 810, SVM by the line 820, and NB by line 830. Based on the adjusted Wald interval, the upper bound of the 95% confidence interval for the balanced classification accuracy of each mental state on the participant level (320 trials) and the study level (11*320=3520 trials) were 55.45% and 51.65%, respectively. These upper bounds may be used to gauge statistical significance for all analyses. In this example, all three classifiers exceeded chance performance levels for all feature set dimensionalities.

Table I presents the balanced classification accuracies attained by each algorithm at the maximum feature set dimensionality of 20 features. Using the Wilcoxon rank-sum test, the shrinkage LDA algorithm was statistically superior ($p<0.05$) to the NB algorithm for the classification of all three mental states and statistically superior ($p<0.05$) to the SVM algorithm for the classification of fatigue. The NB classifier may thus be omitted from further analysis.

Isolating only non-rest tasks, the Pearson correlation coefficients between task performance and mental state were $r=-0.05$ for fatigue, $r=-0.59$ for frustration, and $r=-0.42$ for attention. The negative correlation between frustration and task performance indicates that frustration was experienced by participants when they were unable to solve a problem. The negative correlation between attention and task performance seems unexpected, but is actually a consequence of the experimental protocol; participants reported higher attention levels for tasks that they did not solve correctly because they were focused for the entire duration of the associated trials. When participants solved tasks easily, they rested for the majority of the trial and thus reported a lower attention level. This reflects the decision to focus on mental state for the entire trial rather than simply the task period.

Table II lists the accuracy of task performance for each participant. The accuracy ranged is between 23.3% and 42.1%. The Pearson correlation coefficients between task performance and the accuracy of mental state detection were $r=-0.05$ for fatigue, $r=-0.05$ for frustration, and $r=0.36$ for attention.

TABLE 2

| Task performance for all participants | | | | | | | | | | | |
|---|---|---|---|---|---|---|---|---|---|---|---|
| | Participant | | | | | | | | | | |
| | 1 | 2 | 3 | 4 | 6 | 6 | 7 | 8 | 9 | 10 | 11 |
| Task Accuracy (%) | 42.1 | 42.1 | 23.3 | 34.2 | 41.7 | 32.9 | 33.3 | 35.0 | 32.9 | 32.5 | 26.7 |

TABLE 1

Mean and standard deviation of balanced classification accuracy across all participates for each mental state using 20-feature shrinkage LDA, SMV an NB classifiers.

| Classifier | Fatigue | Frustration | Attention |
|---|---|---|---|
| LDA (Binary) | 74.8 ± 9.1 | 71.6 ± 5.6 | 84.8 ± 7.4 |
| SVM | 73.4 ± 9.4 | 71.1 ± 5.2 | 84.4 ± 7.4 |
| NB | 70.6 ± 9.5 | 68.6 ± 5.6 | 82.5 ± 8.3 |

Figure 9:
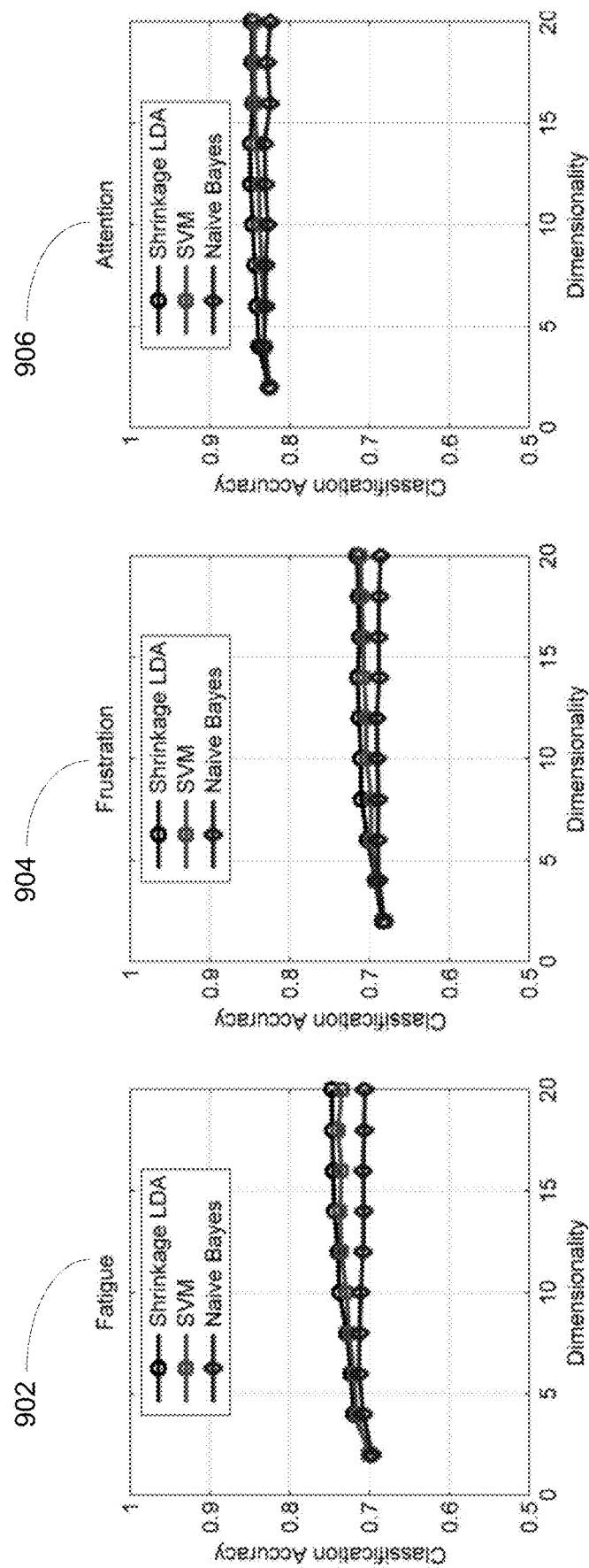
FIG. 9 illustrates, in graph diagrams, the balanced classification accuracy for each participant and mental state using both the shrinkage LDA and SVM classifiers, in accordance with some embodiments.

FIG. 9 illustrates, in graph diagrams, the balanced classification accuracy for each participant and mental state using both the shrinkage LDA and SVM classifiers, in accordance with some embodiments. A comparison between 20-feature SVM and shrinkage LDA classification for each participant for each mental state (fatigue 902, frustration 904, attention 906) is shown. In this example, balanced classification accuracies using both shrinkage LDA and SVM exceeded chance levels for all participants and mental states. Since the shrinkage LDA classifier exhibited the highest balanced classification accuracies for all three mental states, it may be selected for further analysis.

In the embodiment, pearson correlation coefficients of $r=0.13$, $r=0.03$, and $r=0.57$ were exhibited between self-reported fatigue and self-reported frustration, self-reported fatigue and self-reported attention, and self-reported frustration and self-reported attention, respectively. Perceived difficulty exhibited Pearson correlation coefficients of $r=0.03$ with fatigue, $r=0.55$ with frustration, and $r=0.53$ with attention, indicating that task difficulty affected mental state. However, these correlations are sufficiently low to rule out the possibility that classification performance reflected only task difficulty.

Across all participants, the following changes were observed on the relevant PANAS-X subscales between the beginning and the end of the session—from 23.8 to 20.2 for positive affect; from 11.5 to 12.3 for negative affect; from 9.5 to 10.6 for fatigue; and from 11.4 to 9.2 for attention. Thus, participants appeared to experience increasing fatigue and negative affect and decreasing attention and positive affect during the study.

A physiological understanding of changes in fatigue, frustration, and attention may be sought through an analysis of the most frequently selected features for detection of all three states. The original EEG feature set comprised 450 features, each of which represented the spectral power at one electrode 52 within a specific frequency range. The frequency of feature selection may computed for each of these original features as follows. Within the 10×10 repeated cross-validation, 100 classifiers may be trained for each mental state. Each of these classifiers may be trained using a reduced set of features selected by an FCBF. Due to the clustering algorithm employed, each feature used for classification was the sum of some set of original features. The feature selection frequency for each original feature may be defined as the proportion of classifiers for which that original feature was used to compute one of the features used for classification. These feature selection frequencies may then be averaged across all participants to determine which features, electrodes 52, and frequencies are most predictive of changes in each mental state.

Figure 10:
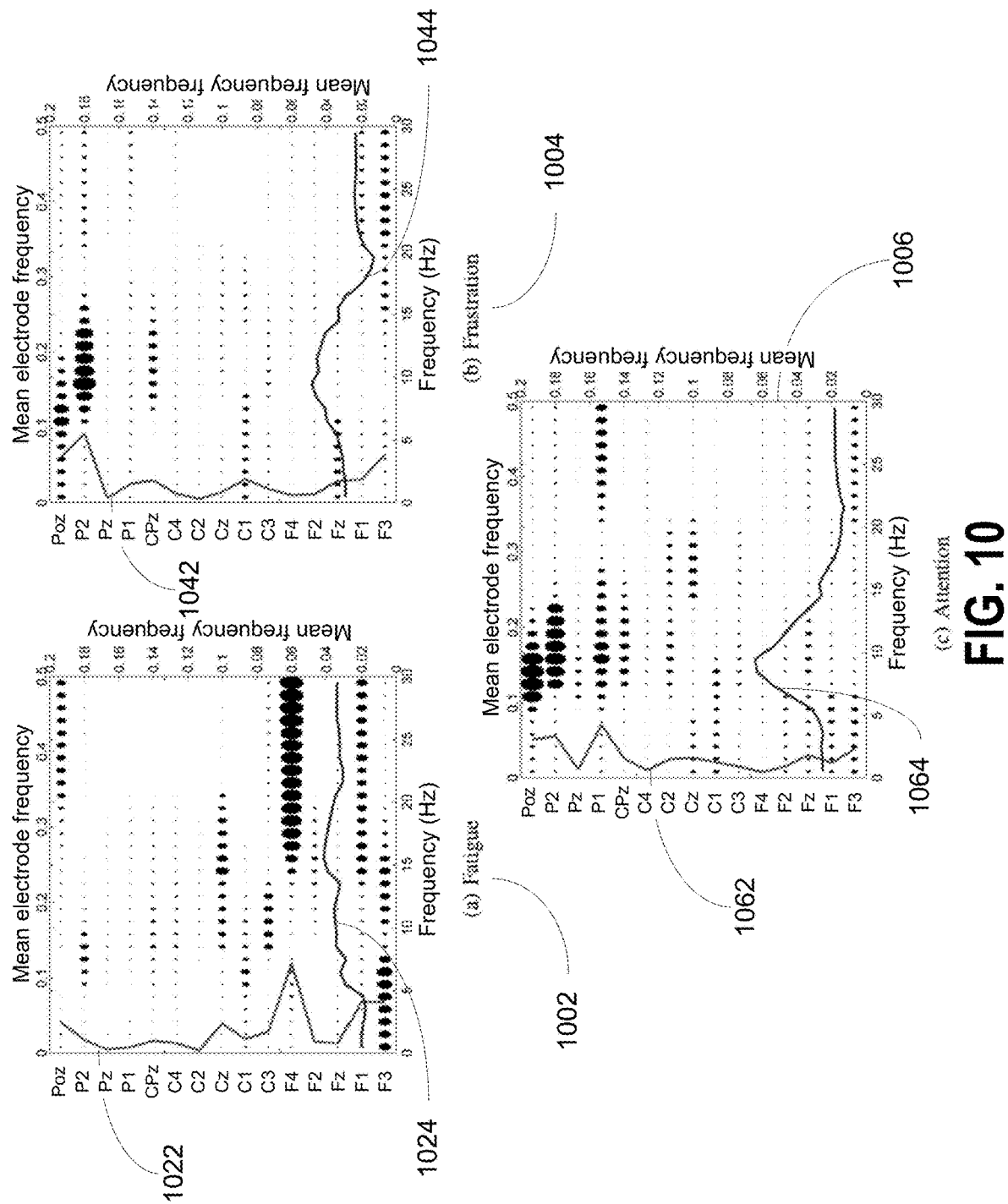
FIG. 10 illustrates, in graph diagrams, feature selection frequency for each feature and mental state, in accordance with some embodiments.

FIG. 10 illustrates, in graph diagrams, feature selection frequency for each feature and mental state, in accordance with some embodiments. Frequencies and electrode locations for predicting changes in (a) fatigue 1002, (b) frustration 1004, and (c) attention 1006 are shown. Each feature is represented by an oval at the appropriate point on the grid, with the spectral frequency on the x-axis and the electrode 52 on the y-axis. I.e., for each feature, the value on the x-axis represents spectral frequency and the value on the y-axis represents cortical location. The size of the oval represents the frequency of feature selection, with larger ovals representing features that were selected more frequently. I.e., the size of each oval represents how frequently that feature was used for classification across all participants on average. Fatigue was most frequently classified using features from the frontal electrodes within the delta, theta, alpha, and beta frequency bands. Frustration was most frequently classified using alpha band features from the posterior electrodes and beta band features from the frontal electrodes. Attention was most frequently classified using alpha band features from the posterior electrodes.

The vertical 1022, 1042, 1062 and horizontal 1024, 1044, 1064 lines represent the average feature selection frequency for all features from the same electrode 52 and frequency, respectively. This visualization may be obtained using the results from 2-feature shrinkage LDA classification of mental state to ensure that only the most predictive features are identified.

Clear differences can be observed between mental states. The features used for fatigue detection most commonly originated from the frontal and central electrodes, particularly those offset from the midline of the cortex. There was a broad range of frequencies amongst these features, including alpha band activity from the central electrodes and activity from all four major frequency bands from the frontal electrodes. Both frustration and attention were frequently classified using features that represented alpha band activity from the posterior electrodes, although frustration detection was also dependent upon features from some other electrodes in the central and frontal regions.

Figure 11:
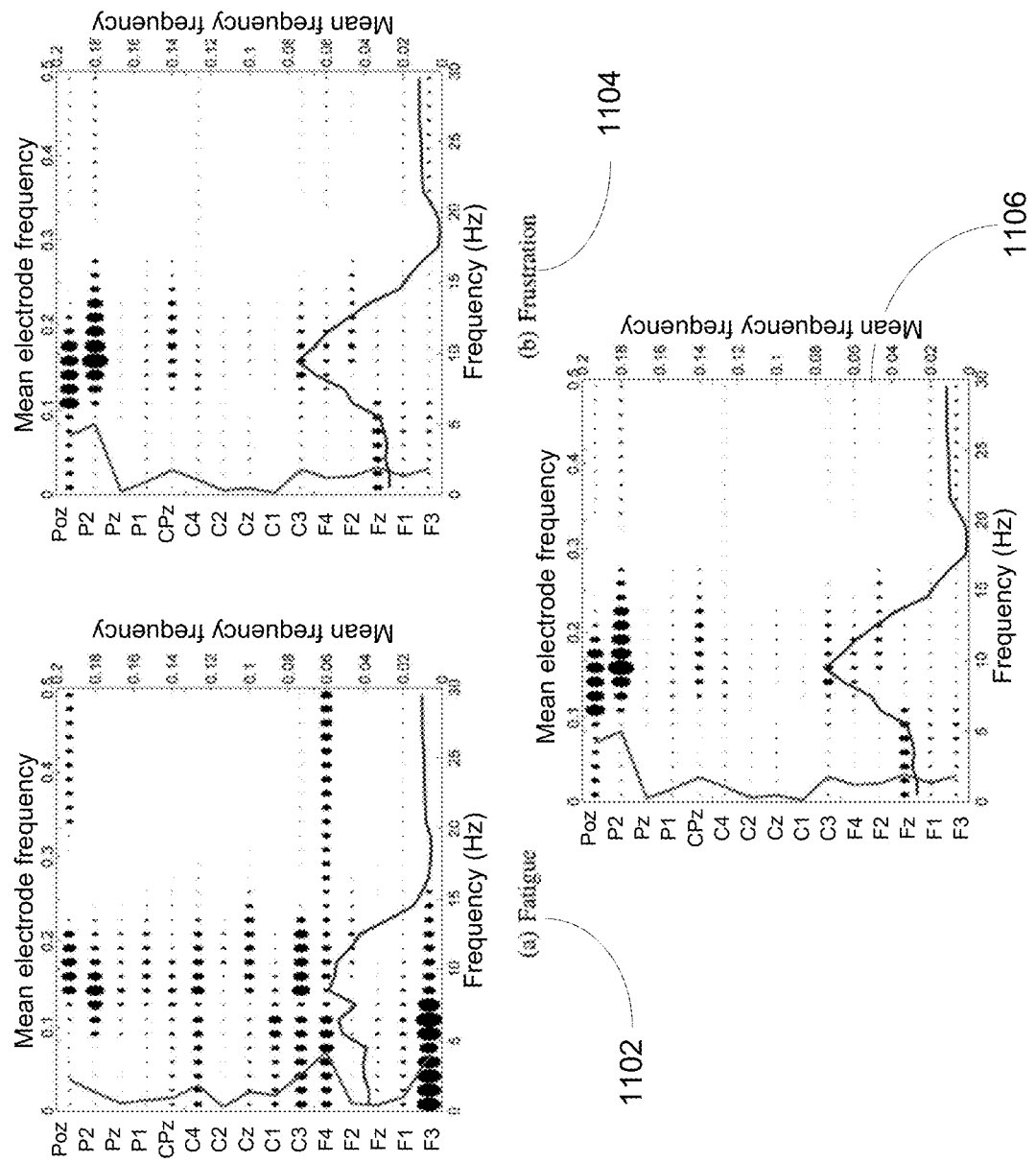
FIG. 11 illustrates, in graph diagrams, feature selection frequency for each feature and mental state, in accordance with some embodiments.

The linear backward model specified by the shrinkage LDA classifier may be transformed into a linear forward model, allowing more direct interpretation of the cortical areas affected by changes in each mental state. The results of this linear forward analysis are depicted in FIG. 11, and corroborate those depicted by FIG. 10, again highlighting the importance of the frontal electrodes for fatigue detection and the posterior electrodes for frustration and attention detection. FIG. 11 illustrates, in graph diagrams, feature selection frequency for each feature and mental state, in accordance with some embodiments. Frequencies and electrode locations for predicting changes in (a) fatigue 1102, (b) frustration 1104, and (c) attention 1106 as quantified using a linear forward analysis are shown in FIG. 11.

The extreme electrode dependence of mental state classification depicted by FIG. 10 encouraged an investigation of the effects of electrode removal on balanced classification accuracy. Classification may be performed using 20-feature shrinkage LDA for six different subsets of electrodes, each of which may be compared to the full set of 15 electrodes 52. These subsets are summarized in Table 3. The feature set derived from each electrode subset may be reduced using feature clustering and a FCBF before classification.

TABLE 3

Electrode subsets. Classification may be performed independently for each subset to gauge the effects of electrode removal.

| Label | Electrodes |
| --- | --- |
| F | Fz, F1, F2, F3, F4 |
| C | Cz, C1, C2, C3, C4 |
| P | CPz, Pz, POz, P1, P2 |
| FC | F U C |
| FP | F U P |
| CP | C U P |
| FCP | F U C U P |

Figure 12:
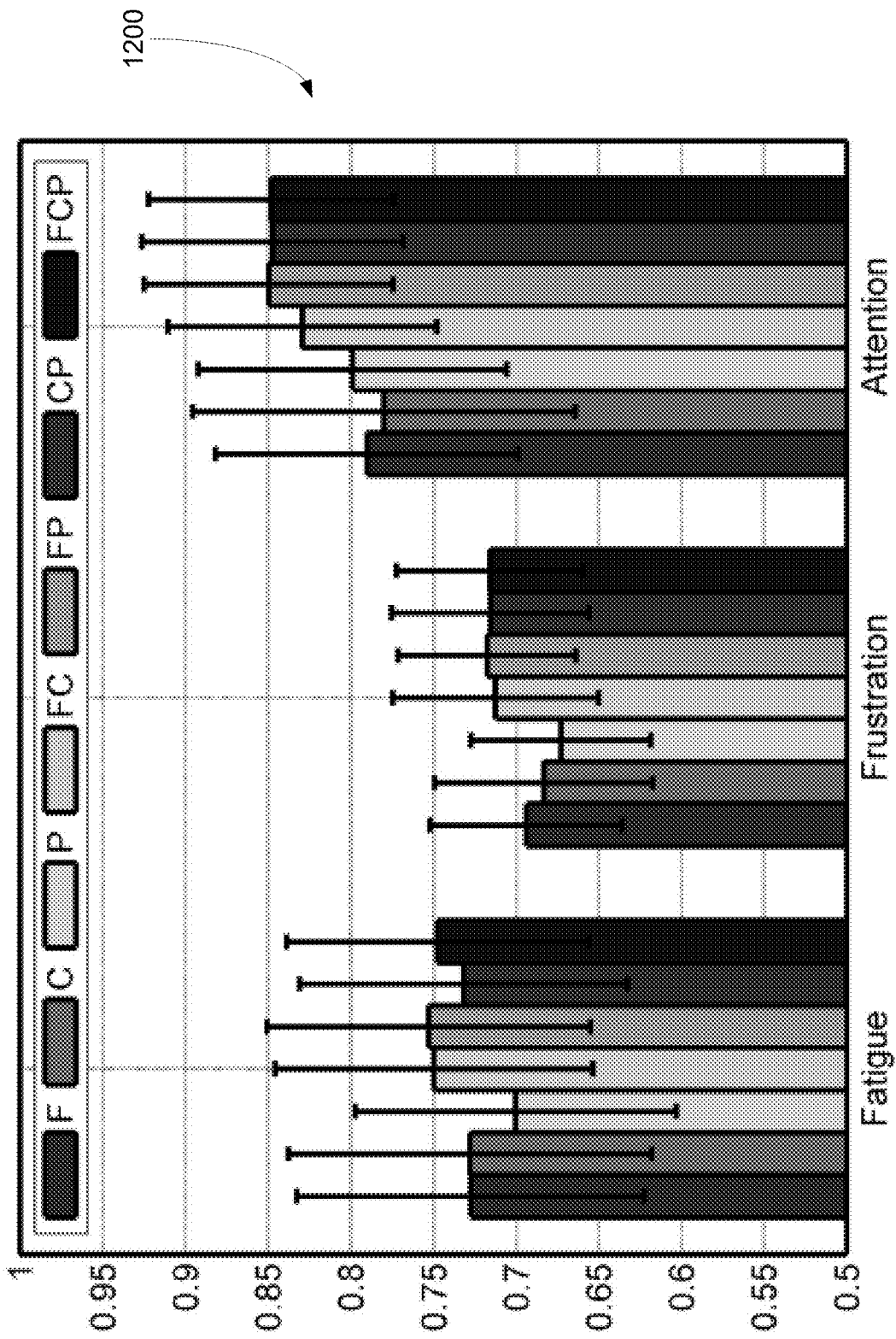
FIG. 12 illustrates, in a graph diagram, an example of balanced classification accuracies attained using each electrode subset for each mental state, in accordance with some embodiments.

FIG. 12 illustrates, in a graph diagram, an example of balanced classification accuracies attained using each electrode subset for each mental state 1200, in accordance with some embodiments. FIG. 12 shows balanced classification accuracies attained using different subsets of the original feature set for each mental state. Table 3 provides a list of electrodes 52 included in each subset. Comparisons may be conducted between classification results using the Wilcoxon rank-sum test. In this embodiment, there were no electrode subsets that provided statistically superior performance to the full FCP set. However, some electrode subsets provided statistically equivalent performance to the FCP set despite their reduced dimensionality. For fatigue detection, the FC subset and the FP subset were statistically equivalent to the FCP set ($p>0.05$). For frustration detection, the FC, FP, and CP subsets were statistically equivalent to the FCP set ($p>0.05$). For attention detection, the FP and CP subsets were statistically equivalent to the FCP set ($p>0.05$). The FCP set was statistically superior ($p<0.05$) to all other electrode subsets for each mental state.

In the previous analyses, every stage of the classification algorithm was participant-dependent. It is of practical interest to investigate methods of rendering this algorithm participant-independent. The generalizability of the algorithm using a participant-level holdout cross-validation may be examined. Data from each participant may be set aside in turn while feature clustering and feature selection are performed using data from all other participants. This allows for an investigation into the consistency of the neural correlates of each mental state across the population of the study. However, individualized shrinkage LDA classifiers may still be trained for each participant to accommodate individual differences in the importance of each selected feature to classification.

Figure 13:
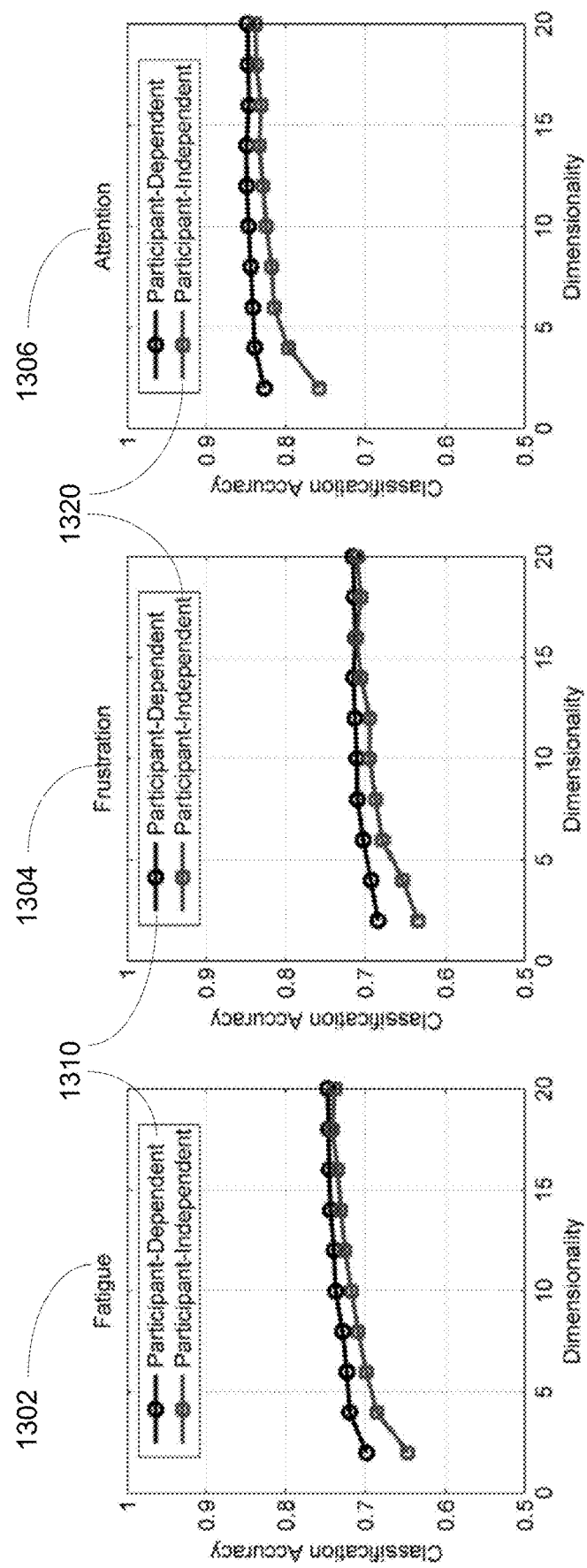
FIG. 13 illustrates, in graph diagrams, the relationship between number of features and balanced classification accuracy for detection of each mental state, in accordance with some embodiments.

FIG. 13 illustrates, in graph diagrams, the relationship between number of features and balanced classification accuracy for detection of each mental state (fatigue 1302, frustration 1304 and attention 1306), in accordance with some embodiments. FIG. 13 shows a comparison between shrinkage LDA balanced classification accuracy after participant-dependent 1310 and participant-independent 1320 feature selection. In the embodiment, the participant-dependent algorithm was more accurate for low feature set dimensionalities, but this difference was less pronounced as the number of features increased. For both algorithms, participant-dependent classifiers may be trained after feature selection. Results from the initial analysis with participant-dependent feature clustering and feature selection are also shown for comparison. Balanced classification accuracies for both classifiers at 20 features are presented in Table 4. At this dimensionality, the participant-dependent algorithm was statistically superior to the participant-independent algorithm for attention detection ($p=0.04$) and statistically equivalent to the participant-independent algorithm for fatigue and frustration detection. The Wilcoxon rank-sum test may be used for all comparisons.

TABLE 4

Mean and standard deviation of balanced classification accuracy across all participants for the 20-feature shrinkage LDA classifier for participant-dependent (PD) and participant-independent (PI) feature selection.

| Classifier | Fatigue | Frustration | Attention |
|---|---|---|---|
| PD | 74.8 ± 9.1 | 71.6 ± 5.6 | 84.8 ± 74 |
| PI | 73.8 ± 8.3 | 71.0 ± 5.8 | 83.8 ± 7.5 |

Figure 14:
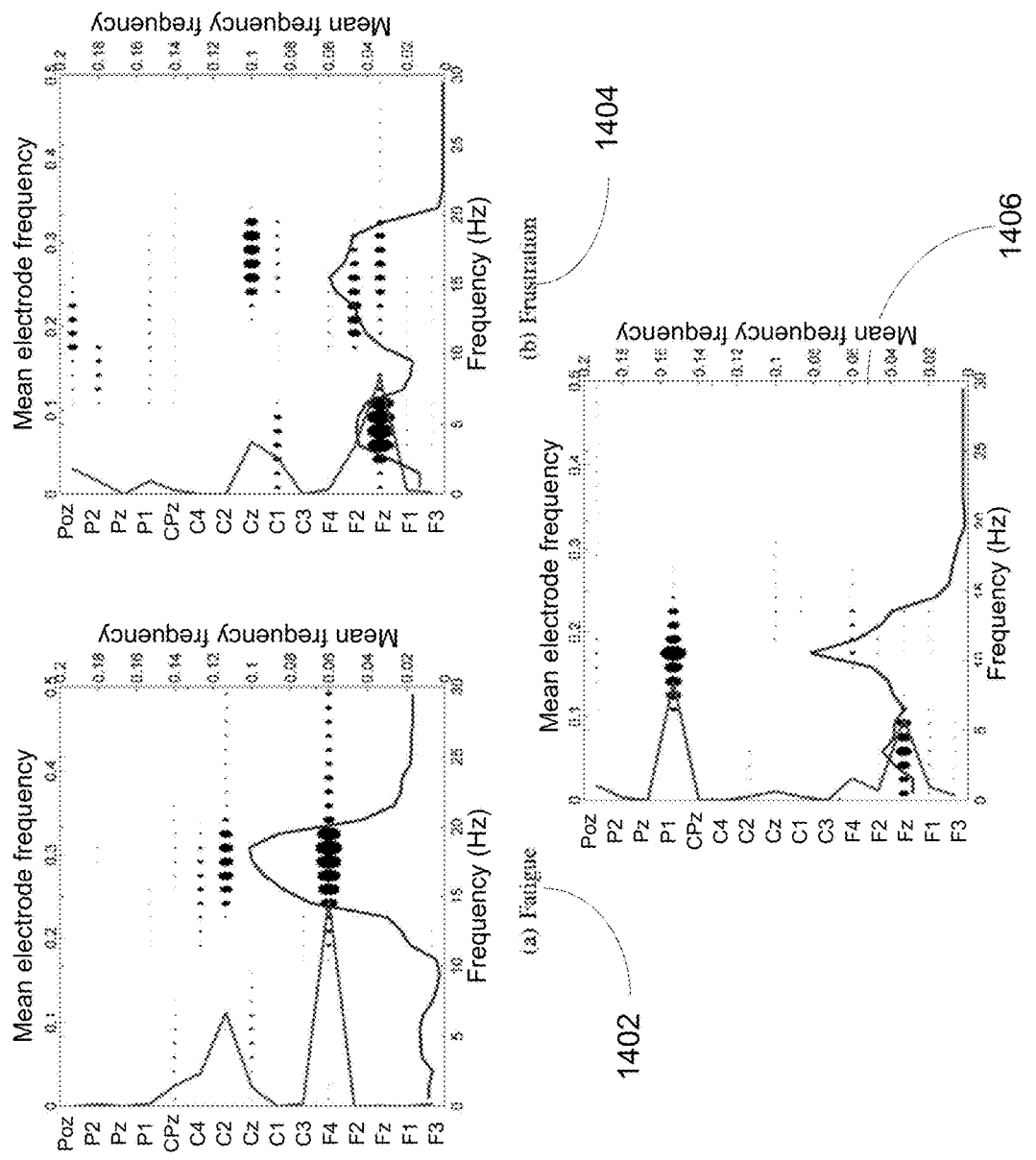
FIG. 14 illustrates, in graph diagrams, results of a feature analysis for the participant-independent analysis, in accordance with some embodiments.

FIG. 14 illustrates, in graph diagrams, results of a feature analysis for the participant-independent analysis, in accordance with some embodiments. FIG. 14 shows frequencies and electrode locations for predicting changes in (a) fatigue 1402, (b) frustration 1404, and (c) attention 1406 when participant-independent feature selection was used. In this example, there appeared to be less diversity for this analysis than for the participant-dependent analysis in FIG. 9 (i.e., there was less variance than exhibited by the participant-dependent case in FIG. 9). Fatigue may be primarily detected using features that originated from F4 at frequencies between 10 and 20 Hz (i.e., using alpha band power from F4), frustration by features that originated from frontal electrodes between 4-7 and 10-20 Hz (i.e., using theta and alpha band power from the frontal electrodes), and attention by features that originated from Fz below 5 Hz and P1 between 7 and 12 Hz (i.e., using delta band power at Fz and alpha band power from P1).

As described above, there is an ability to predict changes in three mental states-fatigue, frustration, and attention—with classification accuracies exceeding 70%. These changes may be detected during the performance of four different mental tasks. Thus, the neuro-electric manifestations of changes in these states may be consistent across a range of cognitive processes. The demonstrated level of mental state detection sets the stage for practical applications of mental state monitoring. In particular, since it has been hypothesized that traditional BCIs are susceptible to changes in mental state, pairing this passive BCI with an active BCI allows for the design of an adaptive BCI that is more robust to fluctuations in mental state.

The above experiment did not show an advantage to using SVM or NB rather than shrinkage LDA for classification. The inferiority of SVM implies that the features used for classification were linearly separable, which aligns with the fact that the metric used for feature selection was a measure of linear correlation. It is considered that the NB algorithm may have performed poorly because the features used for classification were not statistically independent, violating the conditional independence assumption that is central to this classifier.

Although detection was not performed in real-time during this study, the classification algorithm presented here (including feature extraction, feature selection, and classifier training) is not time-intensive. For example, on a computer with a 3.5 GHz processor, full execution of this algorithm required less than 10 seconds. As such, this algorithm is suitable for real-time usage.

Some limitations were present within the embodiment of this study. First, although each session used a unique pseudo-random task order, this task order was not re-randomized for each participant. Thus, each participant completed the same series of tasks, potentially causing some systematic effects on the outcome of the experiment. However, these effects may have had a minimal impact on classification accuracy. High and low-difficulty tasks were dispersed randomly within each session, avoiding any systematic time-based effects. Furthermore, participants each had unique reactions to each series of tasks based on their performance, their aptitude for each task, and their initial mental state at the beginning of the session. Second, participants were provided with visual feedback regarding task performance that may have affected the self-reported ratings (e.g., by increasing frustration) and induced EEG fluctuations that amplified or attenuated those produced by changes in mental state. It is believed that the effects of the limitations present within the study are small in magnitude, as the mental tasks used, and thus the feedback provided, varied throughout the study.

As described above, in an embodiment, the subjective experience of the user may be modeled, as captured by their self-reported ratings of fatigue, frustration, and attention. Two disadvantages of this approach were the inability to ensure balanced target classes for each mental state and the potential inaccuracy of self-reported ratings. The class reduction approach helped mitigate both of these issues—class balance was improved by agglomerating scarcely represented classes with more frequently observed classes, and the data-driven nature of the class reduction algorithm helped supplement the ground truth provided by the self-reported ratings. This had the effect of reducing the classification problem from five classes to two, comparing low and high values for each state.

Although this approach is useful, it is also an artificial interpretation of naturally continuous mental states. Some EEG-based fatigue studies have employed three-class models, and moving in this direction for all three states may be valuable during future integration with an active BCI. Much of the raw data collected during this experiment indicates the viability of such an approach. FIG. 7 displays a simple two-dimensional interpretation of the different self-reported attention levels for Participant 1 as data reduction was performed. Even in such a low-dimensional space, it is possible to identify a continuous trend from low to high attention levels. This trend was seen across all participants and for all mental states.

This underlying structure suggests that with more training data it may be possible to increase the sensitivity of the algorithms detailed above. This could be achieved either through a multi-class problem where each mental state is approximated with three or more states, or a regression-based approach where the concept of classes is discarded and each mental state is estimated on a continuous scale. An alternative data reduction algorithm may be designed that automatically clusters redundant classes without iterating until the classification problem becomes binary. A preliminary analysis of a multi-class approach may be performed by adaptively removing any scarce (i.e., class frequency less than 5%) classes independently for each participant and using LDA to perform classification of this two-to-five class data. Such a preliminary analysis provides classification accuracies of 59.9% for fatigue (chance level 35.9%), 38.9% for frustration (chance level 31.8%), and 36.4% for attention (chance level 24.8%). These results exceeded chance levels ($p<0.05$) for all mental states, encouraging further investigation of this approach.

EEG is a coarse modality for an analysis of the cortical regions in which changes in mental state manifest, particularly after feature clustering has been performed. However, it is worthwhile to summarize the results detailed above and relate them to previous findings. Based on an analysis of the most frequently selected features in FIG. 9, it may be concluded that changes in fatigue manifested within delta, theta, alpha, and beta band activity in the frontal electrodes. On the other hand, frustration detection was most dependent upon posterior alpha band activity and frontal beta band activity, while attention detection relied heavily upon posterior alpha band activity. Participant-independent detection of changes in mental state generally relied upon similar features, particularly for fatigue (frontal alpha and beta) and attention (posterior alpha) detection.

The relationships identified for fatigue detection are reasonably consistent with previous literature. The onset of fatigue has been characterized by an increase in the ratio of slow wave to fast wave EEG, potentially explaining why features from most frequency bands were used for classification in the participant-dependent case. It is understood that alpha activity across the cortex and theta activity within the centro-frontal region of the cortex correlated with subjective sleepiness, and that differences in spectral power within these regions and frequency ranges were predictive of large modulations in fatigue. The above results confirm these relationships while also indicating that these changes in cortical activity can be used for single-trial prediction of small fluctuations in subjective fatigue. It is possible that other cortical areas may also be implicated in the modulation of fatigue levels.

While no existing studies have investigated EEG-based frustration detection, some studies have elucidated the roles of the prefrontal cortex and the parietal lobe in frustration, lending credence to the above observations. There is also support for the importance of delta and theta band activity at Fz for frustration detection. The anterior cingulate cortex (ACC) plays an important role in performance monitoring and may have been measurable at Fz. Furthermore, this cortical region and frequency range are also affected by the error-related potential, which was likely produced during this study when participants performed challenging mental tasks and were aware that they were making mistakes.

Most existing studies regarding the neural basis of attention have focused on sustained vigilance tasks, which may not generalize perfectly to the protocol described above. However, one recent study found that failure in a vigilance task may be predicted by an increase in alpha activity over parieto-occipital regions. This connection was also observed during this study, as both the participant-dependent and participant-independent analyses found that parieto-occipital alpha activity was a strong predictor of fluctuations in attention level. Moreover, the importance of fronto-parietal activity for attention classification is supported by the presence of the dorsal attention network within these regions of the cortex.

Classification results following the removal of some electrodes from the feature set (see FIG. 11) are encouraging for the design of practical passive BCIs. For all three mental states, reduced subsets of electrodes yielded classification accuracies statistically equivalent to those attained using the full FCP set.

This is encouraging, as the ability to reliably detect fluctuations in mental state with just a few EEG electrodes may allow mental state monitoring to be more easily integrated with practical systems. Data-driven methods of constructing electrode subsets, rather than simply using electrodes from one cortical region, may allow interactions between different cortical areas to be used for detection of changes in mental state.

It is interesting to compare the electrode subset classification accuracies from FIG. 11 to the feature selection results in FIGS. 9 and 13. For instance, fatigue detection was typically most accurate for subsets that included the frontal electrodes, as both the participant-dependent and participant-independent feature selection analyses would suggest. A similar relationship is apparent between attention detection and the posterior electrodes. Only for frustration detection is such a relationship not present, as the FC, FP, and CP subsets provided extremely similar classification accuracies. This may explain the inconsistency between the participant-dependent feature selection analysis (which implicated the posterior electrodes) and the participant-independent analysis (which implicated the frontal electrodes) for frustration detection. It is possible that fluctuations in frustration manifest over a wider cortical region than fluctuations in fatigue and attention.

It is noted that the central electrodes do not appear to unduly influence classification for any mental state. This observation suggests that the motor movements required to answer the mental arithmetic, anagram solution, and grid-recall tasks did not produced event-related synchronization and desynchronization in these electrodes. Since accurate performance was maintained even when the central electrodes were removed from the analysis, it is clear that actual fluctuations in mental state were detected, rather than solely the presence of motor activation.

The usage of participant-independent feature selection had an effect on classification accuracy. This was particularly clear for low feature set dimensionalities, where the difference in classification accuracy between participant-dependent and participant-independent feature selection exceeded 5% for all three mental states. This suggests that there is inter-participant variability in the cortical regions and frequency ranges that are most predictive of changes in mental state. However, the superiority of participant-dependent feature selection became less apparent as feature set dimensionality was increased. When 20 features were used, there were no significant differences between the participant-dependent and participant-independent algorithms for fatigue and frustration. It is possible that there are a few cortical regions and frequencies that are typically useful for classification of each mental state, and increasing the dimensionality of the feature set makes it easier for participant-dependent classifier training to identify the most predictive features within this set for each individual.

The classification accuracies attained for fatigue detection are lower than those reported in previous literature. However, this may have occurred because the protocol described above inherently made detection more difficult. For example, one previous study classified fatigue with 84% accuracy but ignored fatigue levels other than unfatigued and exhausted. Another previous study classified five fatigue levels with 91% accuracy during a 25-hour sleep deprivation study. Yet another previous study attained 97% accuracy but again considered only alert and exhausted conditions. In contrast, the protocol described above considered all fatigue levels rather than solely extreme cases, and the short duration of the study limited the extent to which fatigue could be induced. These characteristics of the protocol made the classification of fatigue much more challenging, leading to reduced classification accuracies. Moreover, using a diverse set of cognitive tasks and including rest periods may also have limited the effects of fatigue. However, these shortcomings were deliberate, as the study was designed with the intent of replicating BCI studies as closely as possible. The results from this study are more practically applicable to future passive BCI development than those from studies with prolonged exhaustion protocols.

For attention detection, the reported classification accuracies described above exceed most of those previously reported (e.g., 57% in one previous study, 76% in another). The results described above are nearly on par with the 89% reported in yet another previous study even though that study differentiated attentive and non-attentive tasks in general rather than fluctuations in attention level across the same set of tasks. The results described above provide a foundation for further investigation of multi-level attention detection. Likewise, the single-trial EEG-based frustration detection system provides a basis for future passive BCI research.

One embodiment of a study described above investigated the ability to detect, on a single-trial basis, fluctuations between low and high values of fatigue, frustration, and attention during the performance of challenging mental tasks. The maximum classification accuracies for these three states were $74.8\pm9.1\%$, $71.6\pm5.6\%$, and $84.8\pm7.4\%$ accuracy, respectively. The above findings suggest the possibility for real-time monitoring of these mental states, leading to hybrid brain-computer interfaces that are capable of detecting functional brain activity as well as neuro-electrical manifestations of the user's psychological disposition.

The above embodiments were described with respect to the change in three possible mental states: fatigue, frustration and attention. EEG data for other mental states can be similarly obtained and classified.

Figure 15:
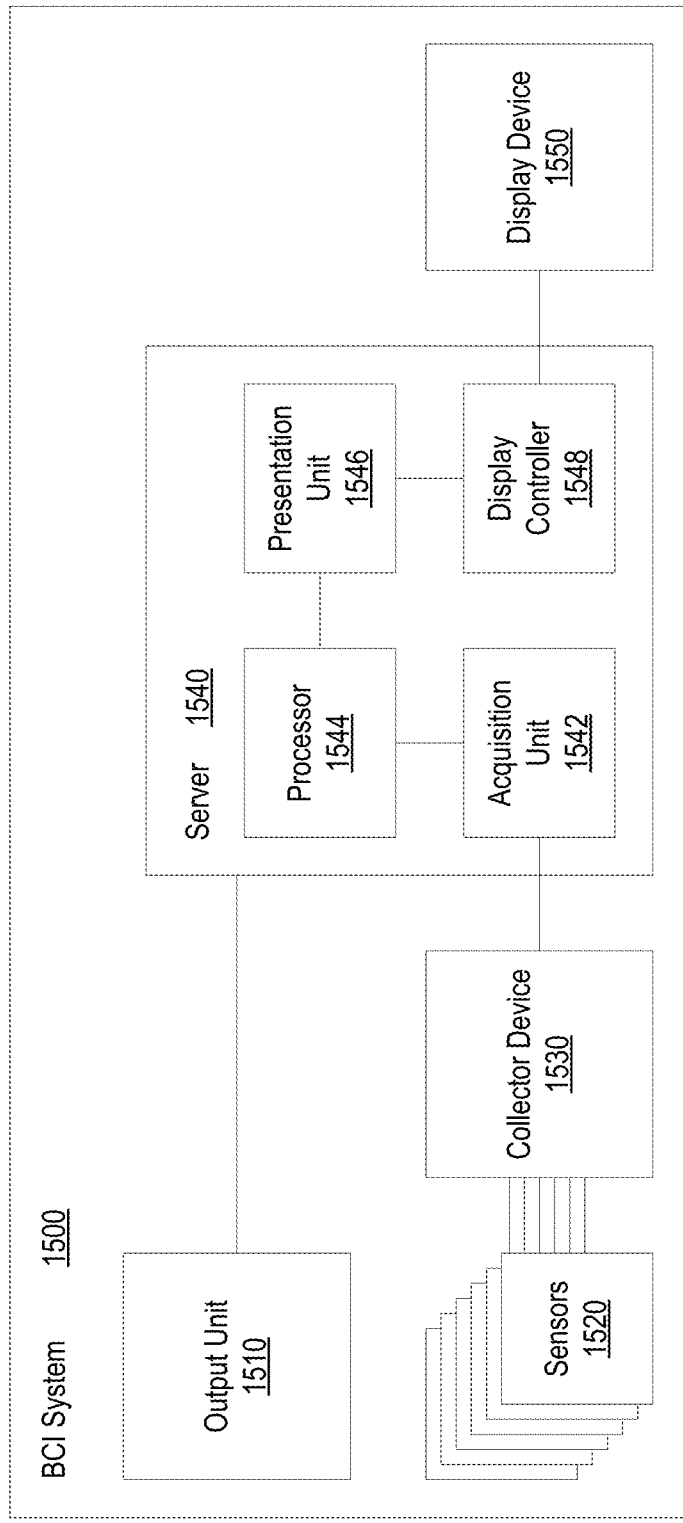
FIG. 15 illustrates, in a component diagram, an example of a BCI system, in accordance with some embodiments.

FIG. 15 illustrates, in a component diagram, an example of a BCI system 1500, in accordance with some embodiments. The BCI system 1500 comprises an output unit 1510 for triggering a series of mental tasks for a patient, a device having a plurality of electrodes 102 to continuously capture real-time raw sensor data from the patient, a server 1540, and a display device 1550 for displaying and updating the BCI with visual elements based on issued control commands from the server 1540. In some embodiments, the BCI system 1500 includes a collector device 1530 coupled to the plurality of sensors for pre-processing the real-time raw sensor data and to correlate the series of mental tasks on a common timeline. In some embodiments, the output unit 1510 and the display device 1550 may be the same component. In some embodiments, the output unit 1510 and the electrodes 102 may comprise the interface application and headset with sensors 130.

The server 1540 comprises an acquisition unit 1542 for receiving electrode 102 data, a processor 1544 for detecting, using the electrode data, real-time changes in brain-state of the patient in response to the series of mental tasks, and a presentation unit 1546 for generating visual elements for an interface in real-time. The processor 1544 uses the sensor data for computing the real-time changes in brain-state of the patient, and for implementing a feature clustering process to account for redundancy in EEG signal features of the sensor data. The visual elements generated by the presentation unit 1546 represent the real-time changes in brain-state of the patient. The server 1540 has a display controller 1548 to issue control commands to update the interface using the generated visual elements. In some embodiments, the acquisition unit 1542 may comprise the data collection unit 122. In some embodiments, the processor 1544 may comprises elements of the classification device 120, such as the classification unit 126, feature selection unit 125, signal processing and feature extraction unit 123. The processor 1544 may perform the steps of the methods 600a, 600b of determining a mental state from multichannel EEG data.

The BCI system 1500 may be used for passive BCI monitoring of a patient in parallel with active BCI monitoring. In one embodiment, the BCI system 1500 may be used in a virtual reality setting. For example, the difficulty level of a game may be dynamically adjusted to an easier level if the brain-state of the user is found to be frustration during the current difficult level. In another embodiment, the BCI system 1500 may be used in a medical/monitoring setting. For example, the brain-state of a patient may be continuously monitored. The brain-state of the patient may be displayed and updated at a nurse station. Generally, the BCI system 1500 may be used when a passive monitoring of the brain-state of a subject is desired.

Figure 16:
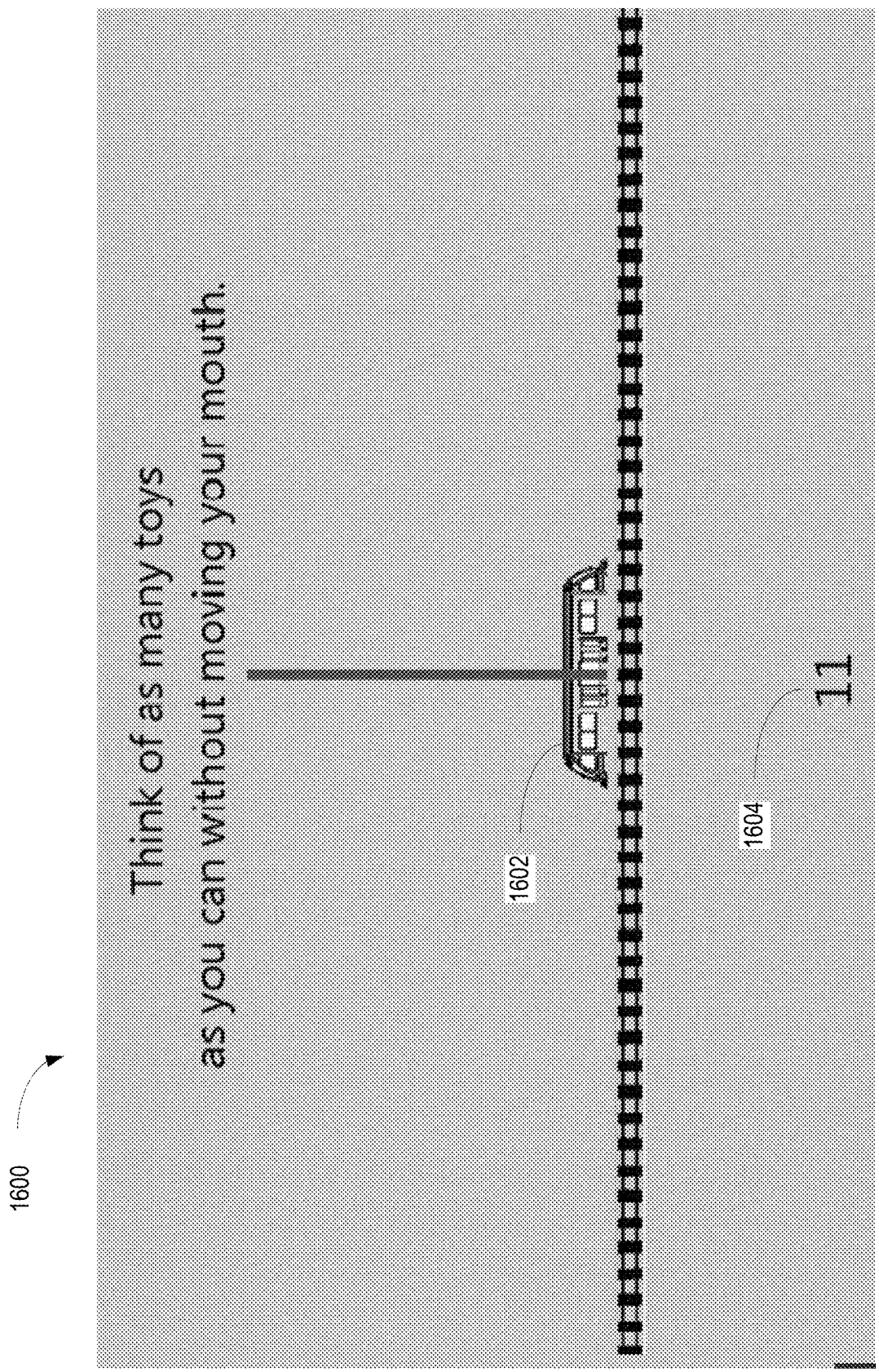
FIG. 16 illustrates, in a screenshot, an example of visual elements, in accordance with some embodiments.

FIG. 16 illustrates, in a screenshot, an example of visual elements 1600, in accordance with some embodiments. In this example, the visual elements 1600 comprise part of a train animation that moves in response to the real-time changes in the brain-state of the patient. For example, a continuous feedback may be provided in the form of a train 1602 that moves to the right or left in response to an increase or decrease in blood flow to the prefrontal cortex, respectively. FIG. 16 is an example of a verbal fluency task where a participant may be instructed to think of as many items as possible in, for example, 20 seconds in the category of "toys". In this example, a countdown timer 1604 is shown at the bottom of the screen. This example involves the use of active BCI monitoring. However, passive BCI monitoring can be applied in parallel to detect the brain-state that the participant would experience during performance of the mental task. For example, the participant may experience frustration if the task is not successful. Such mental state or brain activity would be detected by one or more sensors 1520 (e.g., electrodes 52).

Figure 17B:
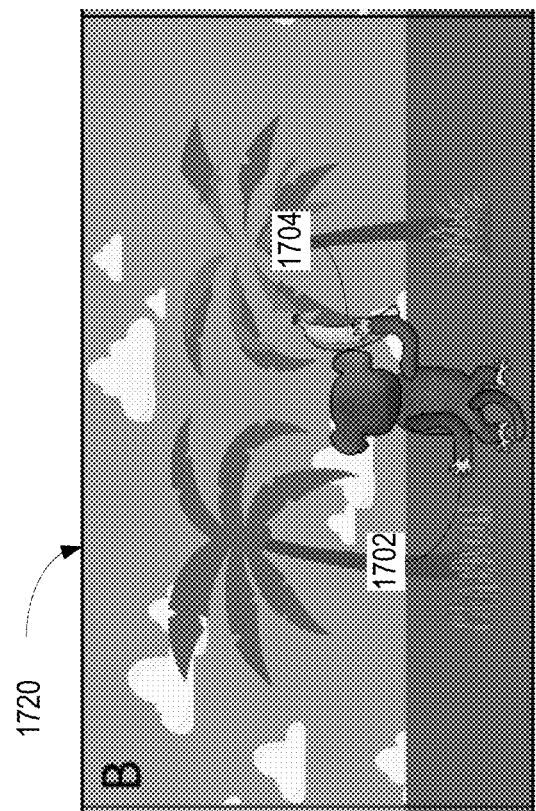
FIGS. 17A to 17C illustrate, in three screenshots, another example of visual elements, in accordance with some embodiments.
Figure 17A:
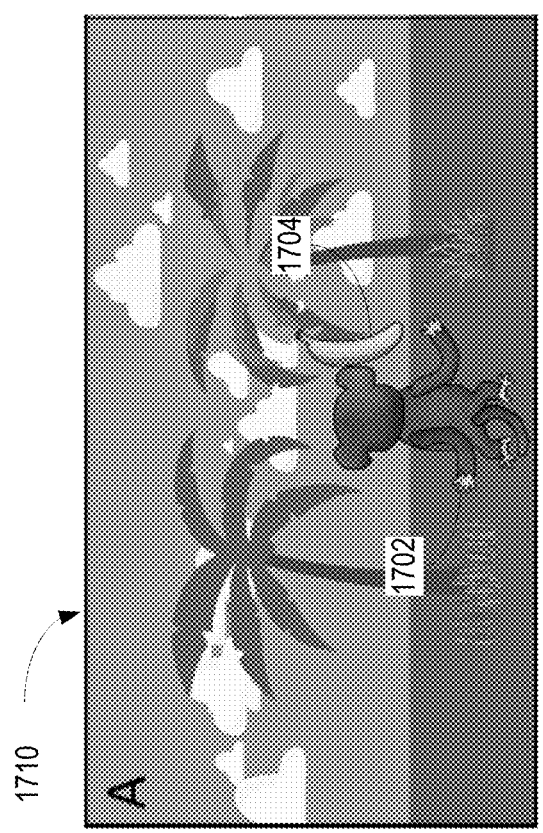
Figure 17C:
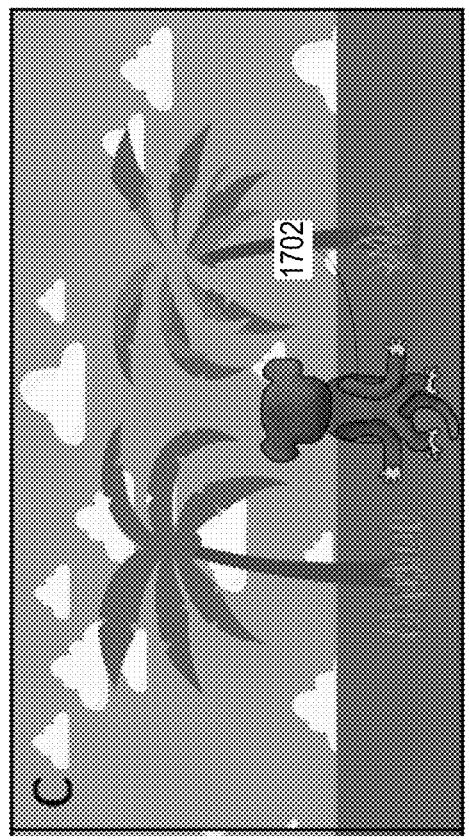

FIGS. 17A to 17C illustrate, in three screenshots, another example of visual elements 1700, in accordance with some embodiments. In this example, the visual elements 1700 comprise part of a game that moves one or more features of a virtual character in response to the real-time changes in the brain-state of the patient. In this example, in screenshot 1710, a banana 1704 appears on the right side cueing right motor imagery (MI). In screenshot 1720, the monkey 1702 reaches the banana 1704 (at the conclusion of the MI task performance period). In screenshot 1730, the monkey 1702 is resting between trials. This example involves the use of active BCI monitoring. However, passive BCI monitoring can be applied in parallel to detect the brain-state that the participant would experience during performance of the mental task. For example, the participant may experience frustration if the task is not successful. Such mental state or brain activity would be detected by one or more sensors 1520 (e.g., electrodes 52).

Figure 18:
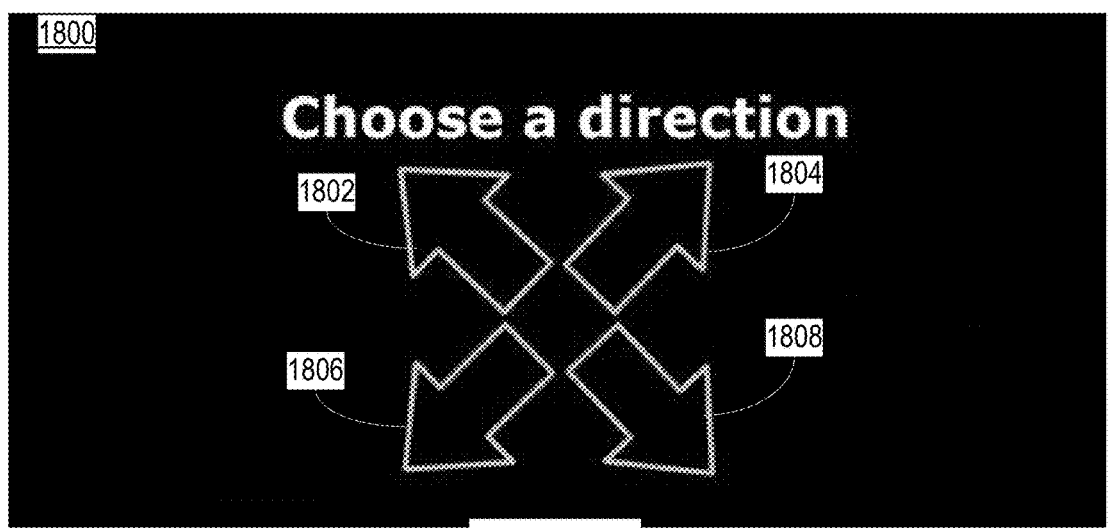
FIG. 18 illustrates, in a screenshot, an example of four directional visual cues, in accordance with some embodiments.

In another example, visual spatial imagery tasks may be employed. For example, visual cues may be displayed on the output unit 1510 to the participant. FIG. 18 illustrates, in a screenshot 1800, an example of four directional visual cues, in accordance with some embodiments. The visual cues comprise an upper-left arrow 1802, an upper right arrow 1804, a lower left arrow 1806 and a lower right arrow 1808. The participant is instructed to choose a direction. A visual cue is presented to the participant. If the visual cue does not match the direct they chose, then the participant is to rest which causes the presentation of another visual cue. If the visual cue does match the direction they chose, then the participant is to visualize the movement of a character in a game.

Figure 19:
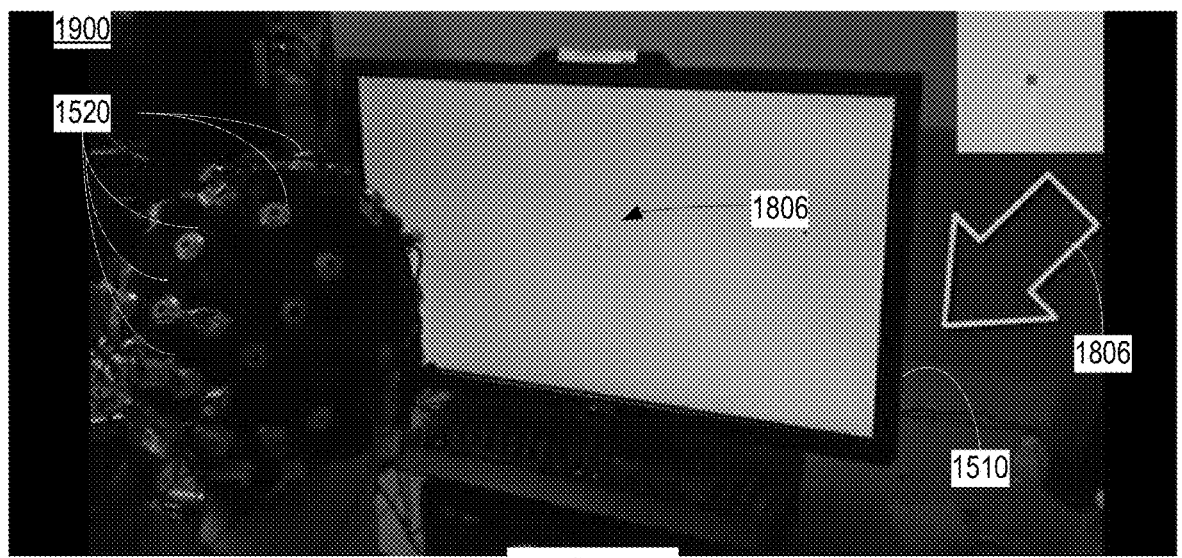
FIG. 19 illustrates, in a screenshot, a participant wearing electrode sensors watching an output unit, in accordance with some embodiments.

FIG. 19 illustrates, in a screenshot 1900, a participant wearing electrode sensors 1520 (i.e., electrodes 52) watching an output unit 1510, in accordance with some embodiments. The output unit 1510 is displaying a visual cue for the direction lower-left 1806. The participate is to visualize a movement of a character in that direction.

Figure 20:
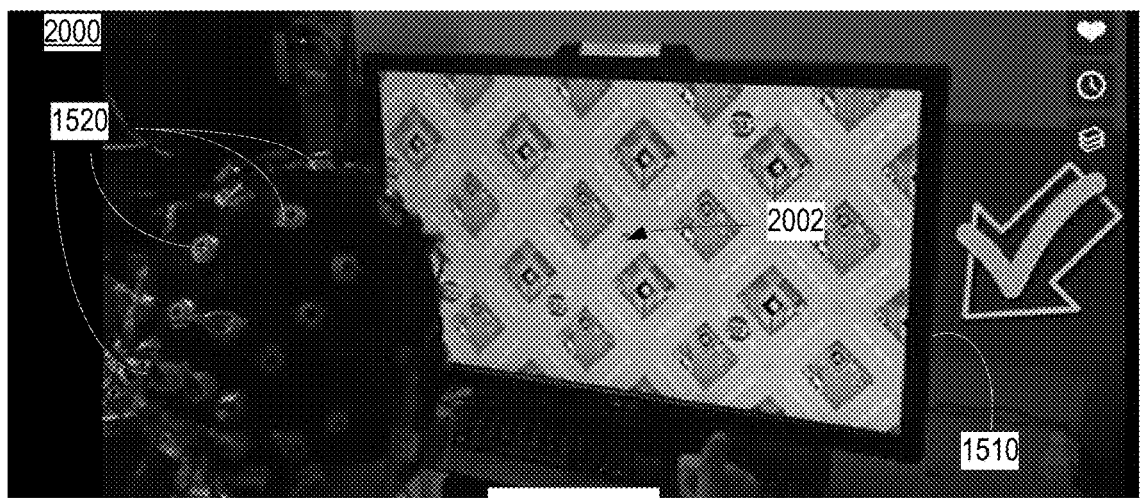
FIG. 20 illustrates, in another screenshot, the participant wearing the electrode sensors watching the display unit, in accordance with some embodiments.

FIG. 20 illustrates, in another screenshot 2000, the participant wearing the electrode sensors 1520 watching the display unit 1550, in accordance with some embodiments. In this example, the display unit is the same monitor as the output unit 1510. Here, the character 2002 is correctly moving in the lower-left direction in response to the participant's visualization. In this example, the brain-state that the participant would experience during visualization would be detected by one or more sensors 1520 (e.g., electrodes 52). The EEG signals would be pre-processed by a collector device 1530 and sent to the acquisition unit 1542. The EEG data would then be sent to the processor 1544 to determine the real-time brain-state of the participant. The presentation unit 1546 receives the brain-state and generates the visual elements of the character 2002 moving along the lower-left direction. The display controller issues control commands to the display device 1550 to update the interface with the visual elements (e.g., have the character 2002 move along the lower-left direction).

The example described in FIGS. 18 to 20 involve the use of active BCI monitoring. However, passive BCI monitoring can be applied in parallel to detect the brain-state that the participant would experience during performance of the mental task. For example, the participant may experience frustration if the task is not successful. Such mental state or brain activity would be detected by one or more sensors 1520 (e.g., electrodes 52).

Figure 21:
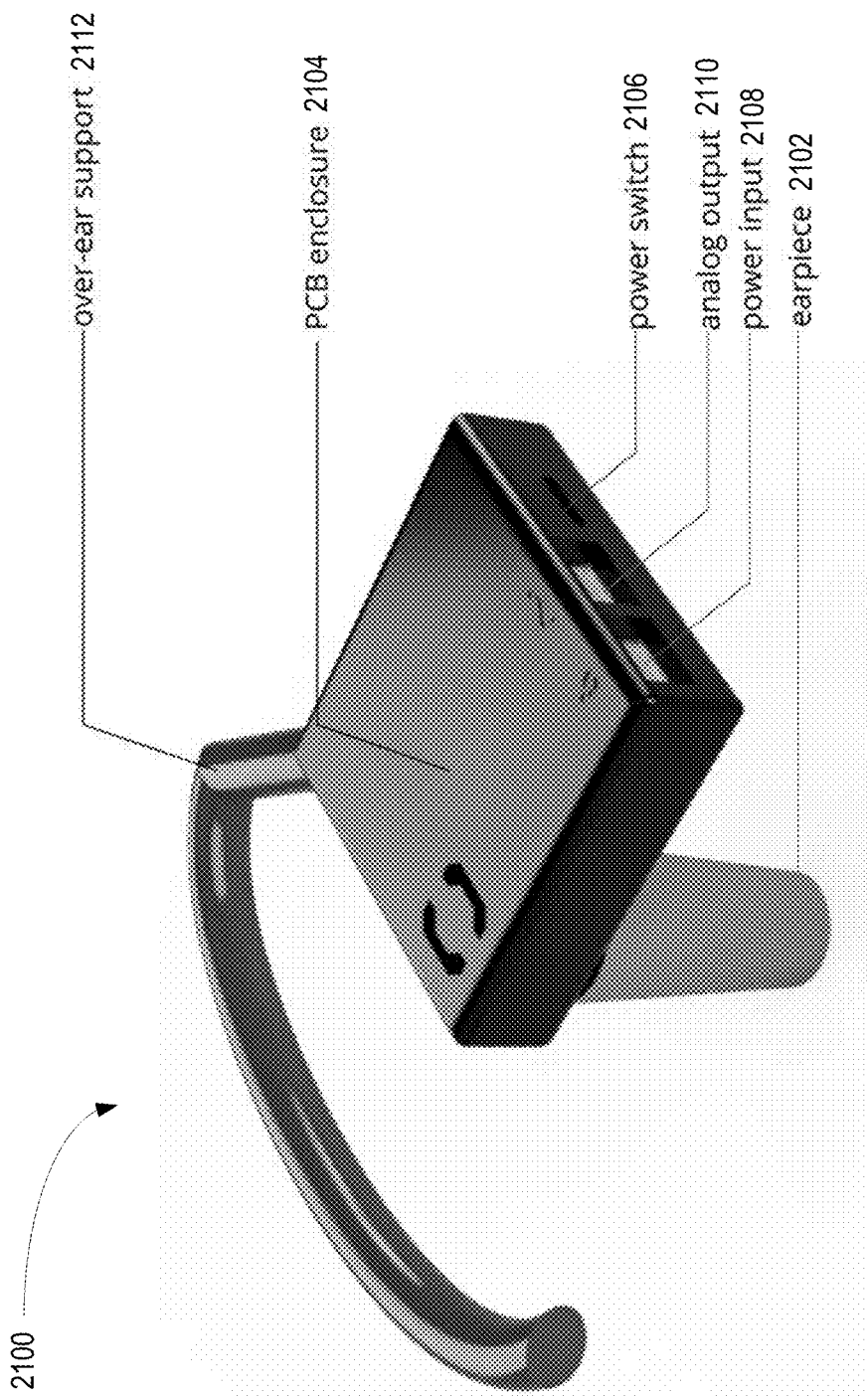
FIG. 21 illustrates, in a three-dimensional rendering, an example of an in-ear EEG device 2100, in accordance with some embodiments.

FIG. 21 illustrates, in a three-dimensional rendering, an example of an in-ear EEG device 2100, in accordance with some embodiments. The in-ear EEG device 2100 comprises an ear-piece 2102, a PCB enclosure 2104, a power switch 2106, and connections for both electrical power input 2108 and analog output 2110. An over-ear support 2112 is placed around the ear-lobe so as to ensure proper placement of the device and enhance comfort over long periods of use. Furthermore, a contiguous hole exists in the earpiece 2102, PCB, and enclosure 2104, which should allow for reduced sound attenuation and enable the wearer to hear their environment.

The in-ear EEG device 2100 may be used in conjunction with the sensors 1520 to collect EEG data from a participant. In some embodiments, the in-ear EEG device 2100 may include two electrodes 102 placed inside the ear-canal (on the ear-piece 2102), along with a reference electrode placed either on the earlobe or the mastoid. In the case of the latter design choice, the reference electrode will follow the curve of the ear-lobe support. These electrodes may serve as the positive and negative inputs of the first-stage operational-amplifier, and may be placed approximately 180 degrees apart on the ear-piece to maximize the differential signal.

Figure 22:
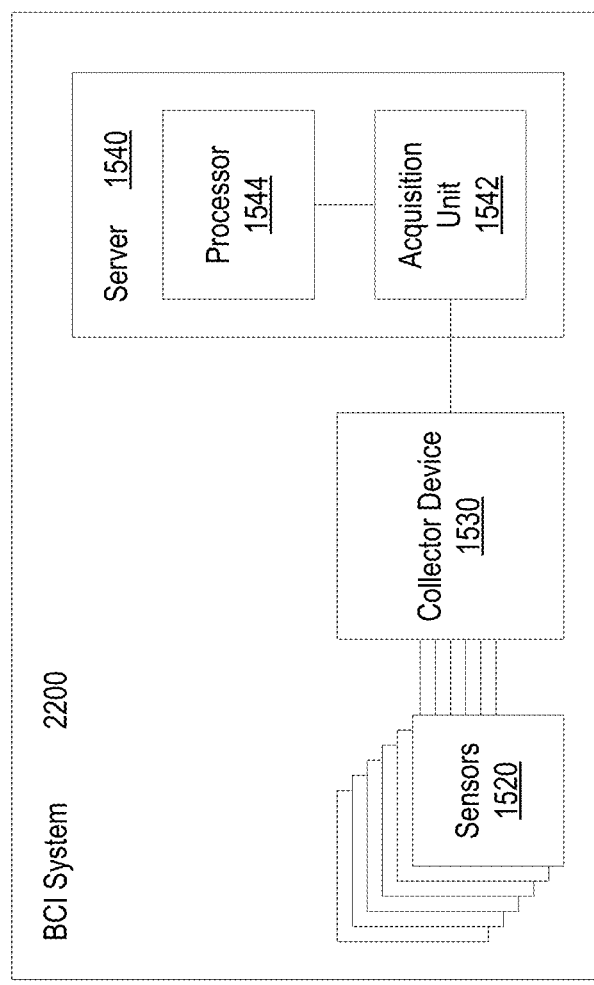
FIG. 22 illustrates, in a component diagram, another example of a BCI system 2200, in accordance with some embodiments.

FIG. 22 illustrates, in a component diagram, another example of a BCI system 2200, in accordance with some embodiments. The BCI system 2200 comprises a device having a plurality of electrodes 102 to continuously capture real-time raw sensor data from a patient and a server 1540. In some embodiments, the BCI system 1500 includes a collector device 1530 coupled to the plurality of sensors for pre-processing the real-time raw sensor data and to correlate the series of mental tasks on a common timeline. In some embodiments, the device having a plurality of electrodes 102 may comprise the headset with sensors 130 or an in-ear EEG device.

The server 1540 comprises an acquisition unit 1542 for receiving electrode 102 data, a processor 1544 for detecting, using the electrode data, real-time changes in brain-state of the patient in response to the series of mental tasks. The processor 1544 uses the electrode data for computing the real-time changes in brain-state of the patient, and for implementing a feature clustering process to account for redundancy in EEG signal features of the sensor data. In some embodiments, the acquisition unit 1542 may comprise the data collection unit 122. In some embodiments, the processor 1544 may comprises elements of the classification device 120, such as the classification unit 126, feature selection unit 125, signal processing and feature extraction unit 123. The processor 1544 may perform the steps of the methods 600*a*, 600*b* of determining a mental state from multichannel EEG data. In some embodiments, the BCI system 2200 may include combinations of one or more other elements of the BCI system 1500.

The BCI system 2200 may be used for passive BCI monitoring of a patient in parallel with active BCI monitoring. In one embodiment, the BCI system 2200 may be used in a virtual reality setting. For example, the difficulty level of a game may be dynamically adjusted to an easier level if the brain-state of the user is found to be frustration during the current difficult level. In another embodiment, the BCI system 2200 may be used in a medical/monitoring setting. For example, the brain-state of a patient may be continuously monitored. The brain-state of the patient may be displayed and updated at a nurse station. Generally, the BCI system 2200 may be used when a passive monitoring of the brain-state of a subject is desired.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. A system for a brain-computer interface (BCI) comprising:
    an output unit configured to trigger a series of mental tasks for a patient, the series of mental tasks comprising a plurality of different mental task types, each mental task type comprising at least two difficulty levels;
    a device having a plurality of electrodes to continuously capture real-time raw electroencephalography (EEG) data from the patient;
    a server having:
        a collector device configured to pre-process the real-time raw EEG data into real-time EEG data;
        an acquisition unit configured to receive the real-time EEG data;
        a processor configured to detect, using the real-time EEG data, real-time changes in EEG activity of the patient in response to the series of mental tasks, and wherein the processor is configured to determine, using the real-time EEG data, one or more of a plurality of mental states of the patient comprising fatigue, frustration, and attention, based on EEG frequency spectra, by:
            generating a set of features based upon a frequency domain analysis of the real-time EEG data;
            reducing the dimensionality of the set of features by implementing a feature clustering process to account for redundancy in EEG signal features of the real-time EEG data; and
            classifying the features into at least one mental state of the plurality of mental states to detect corresponding real-time changes in one or more of the plurality of mental states of the patient in response to the series of mental tasks for the patient;
        a presentation unit configured to generate visual elements for an interface in real-time, wherein the visual elements represent the real-time changes in the EEG activity of the patient or the visual elements of the interface move in response to the real-time changes in the EEG activity of the patient; and
        a display controller configured to issue control commands to update the interface using the generated visual elements; and
    a display device to display and update the interface with the visual elements based on the issued control commands from the server.

2. The system of claim 1, wherein the collector device is coupled to the plurality of electrodes to pre-process the real-time raw EEG data into the real-time EEG data, and wherein the collector device correlates the real-time EEG data to the series of mental tasks in time.

3. The system of claim 2, wherein the processor is further configured to oversample EEG data collected at a current time, such that the EEG data collected at the current time is weighted more heavily than historical EEG data.

4. The system of claim 1, wherein the output unit is configured to attempt to elicit a change in a mental state by a sequential trigger of the series of mental tasks based on a dynamic selection of tasks by the system that is specific to the patient, wherein:
    each mental task is selected from the set of an arithmetic task, an anagram task, and a grid-recall task; and
    each mental task is to be performed within a time period for that mental task.

5. The system of claim 4, wherein:
    the number of difficulty levels for each task type is five; and
    the mental tasks are triggered in pseudo-random order with some clustering of tasks having the lowest difficulty level and tasks having the highest difficulty level.

6. The system of claim 1, wherein each electrode of the plurality of electrodes receives an EEG signal, and wherein to generate the set of features, the processor is further configured to:
    compute a fast Fourier Transform (FFT) for each EEG signal received from each electrode, resulting in a frequency spectrum for each EEG signal; and
    compute a total spectral power within each of a plurality of non-overlapping frequency ranges in each frequency spectrum.

7. The system of claim 6, wherein the non-overlapping frequency ranges comprise one Hz frequency ranges between zero to 30 Hz.

8. The system of claim 6, wherein each computed total spectral power measurement is a feature of the set of features.

9. The system of claim 8, wherein to reduce the dimensionality of the set of features, the processor is further configured to:
    apply a clustering process to group the features generated from the real-time EEG data from each electrode into data-sensitive frequency bands; and
    apply a fast correlation-based filter to select between two and 20 features for classification.

10. The system of claim 9, wherein to classify the features into the plurality of mental states, the processor is further configured to:
    apply a shrinkage linear discrimination analysis to each frequency spectrum of each non-overlapping frequency range of the selected features; and
    determine the plurality of mental states based on the frequency ranges and spectral power corresponding to the selected features.

* * * * *